US008645084B1

(12) United States Patent
Cetinkaya

(10) Patent No.: US 8,645,084 B1
(45) Date of Patent: Feb. 4, 2014

(54) NON-CONTACT MECHANICAL PROPERTY DETERMINATION OF DRUG TABLETS

(75) Inventor: Cetin Cetinkaya, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 1009 days.

(21) Appl. No.: 11/725,963

(22) Filed: Mar. 20, 2007

Related U.S. Application Data

(60) Provisional application No. 60/808,537, filed on May 26, 2006, provisional application No. 60/783,574, filed on Mar. 20, 2006.

(51) Int. Cl.
*G06F 19/00* (2011.01)
*G01M 1/14* (2006.01)

(52) U.S. Cl.
USPC ............................................. 702/39; 73/1.82

(58) Field of Classification Search
USPC ........... 702/39, 19, 23, 28, 33, 40, 56, 81, 84, 702/108, 113, 127, 137, 138–140, 150–153, 702/155–159, 170–172, 182–183; 73/1.82; 324/71.1, 71.3; 250/306, 307, 309; 204/5, 9, 406–409
See application file for complete search history.

(56) References Cited

PUBLICATIONS

Karppinen et al., Ultrasonic Monitoring of Paper and Tablet Coating Stiffness During Layer Formation, 2005 IEEE, pp. 1488-1491.*
Levina et al., Principles and Application of Ultrsound in Pharmaceutical Powder Compression, 2000, Pharmaceutical Research, vol. 17, No. 3, pp. 257-265.*
Varghese et al., Non-Contacting Drug Tablet Monitoring, Feb. 1, 2006, Control engineering: Non-Contact Drug Tablet Monitoring, pp. 1-3.*
Kirsch et al., Nondestructive tablet Hardness Testing by Near-Infrared Spectroscopy: A New and Robust Spectral Best-Fit Algorithm, 1999, Journal of Pharmaceutical and Biomedical Alaylsis 19, pp. 351-362.*
Akseli et al., Real-Time Acoustic Elastic Property Monitoring of Compacts During Compaction, 2008, J. Pharm Innov, pp. 134-140.*
Roberts et al., Mechanical Property Predictions for Polymorphs of Sulphathiazole and Carbamazepine, 2000, European Journal of Pharmaceutical Sciences 9, pp. 277-283.*
Varghese et al., Non-Contact Techniques for Drug Tablet Monitoring, Oct. 4, 2005, Pharmaceutical Processing, 7 pp.*
Ketolainen et al., Photoacoustic Evaluation of Elasticity and Integrity of Pharmaceutical Tablets, 1995, International Journal of Pharmaceutics 125, pp. 45-53.*

(Continued)

*Primary Examiner* — Toan Le
(74) *Attorney, Agent, or Firm* — George R. McGuire; Bond Schoeneck & King, PLLC

(57) ABSTRACT

A non-contact/non-destructive technique for determining the mechanical properties of coated drug tablets is presented. One method is to detect, monitor and characterize a drug tablet during compaction by means of transmitting and receiving acoustic waves into the powder core, as it is formed in a press (compactor), via transducers embedded in the compactor die and punches. An iterative computational procedure is shown that extracts the mechanical properties of the coated tablet from a subset of its measured resonance frequencies. Sensitivities of the resonance frequencies to changes in the tablet mechanical properties is illustrated and discussed. These non-destructive techniques require no physical contact with the tablet and operate in the microsecond time-scale. Therefore, they can be employed for rapid monitoring and characterization applications.

22 Claims, 24 Drawing Sheets

(56) References Cited

PUBLICATIONS

Levina et al., Principles and Application of Ultrasound in Pharmaceutical Powder Compression, 2000, Pharmaceutical Research, vol. 17, No. 3, pp. 257-265.*
Morse P.M., Ingard K.U., Theoretical Acoustics, Princeton University Press, 1968.
Krautkramer J., Krautkramer K., Ultrasonic Testing of Materials, Springer-Verlag, 1990.
Carlin, Brian A.C., The Future of Compaction Pharmacentical Tableting in the Twenty-First Century, Pharmaceutical Technology, Jun. 2004 (40-45).
Varghese I., Ban L., Peri M.D.M., Li C., Subramanian G., Cetinkaya C., Non-Contact Drug Tablet Monitoring, Control Engineering, Feb. 2006; vol. 53 (2), 2006.
Varghese I., Cetinkaya C., Non-contact Photo-Acoustic Defect Detection is Drug Tablets, Journal of Pharmaceutical Sciences, vol. 96, No. 8, Aug. 2007.
Berkovich, E. S., Three-Faceted Diamond Pyramid for Micro-Hardness Testing, Industrial Diamond Review, Jun. 1951,vol. 11, No. 127 (129-132).
Jetzer W., Leuenberger H., Sucker H., The Compressibility and Compatibility of Pharmaceutical Powders. Pharmaceutical Technology, 1983, vol. 7 (33-39).
Fell J.T., Newton, J.M., Tensile Strength of Lactose Tablets. The Journal of Pharmacy and Pharmacology, 1968, vol. 20 (656-659).
Fell J.T., Newton, J.M., The Prediction of the Tensile Strength of Tablets. The Journal of Pharmacy and Pharmacology, 1970, vol. 22 (247).
Densities of Pharmaceutical Powders, Blends, Dry Granulations, and Immediate-Release Tablets. Pharmaceutical Technology, Apr. 2003, vol. 27 (64-80).
Payne R.S., Roberts R.J., Rowe R.C., McPartin M., Bashall A., The Mechanical Properties of Two Forms of Primidone Predicted from their Crystal Structures. International Journal of Pharmaceutics, 1996, vol. 145 (165-173).
Roberts R. J., Rowe R.C., The Young's Modulus of Pharmaceutical Materials. International Journal of Pharmaceutics, 1987, vol. 37 (15-18).
Bassam F., York P., Rowe R.C., Roberts R. J., Young's Modulus of Powders Used as Pharmaceutical Excipients. International Journal of Pharmaceutics, 1990, vol. 64 (55-60).
Rigdway K., Aulton M.E., Rosser P.H.,The Surface Hardness of Tablets, Jounal of Pharmacy and Pharmacology, 1970, vol. 22 (705-785).
Felton L.A., Shah N.H., Zhang G., Infeld M.H., Malick A.W., McGinity J.W., Physical-Mechanical Properties of Film-Coated Soft Gelatin Capsules. International Journal of Pharmaceutics, 1996, vol. 127 (203-211).
Stanley P., Rowe R.C., Newton J.M., Theorectical Considerations of the Influence of Polymer Film Coatings on the Mechanical Strength of Tablets. Journal of Pharmacy and Pharmacology, 1981, vol. 33 (557-560).
Gutierrez-Rocca J.S., McGinity J.W., Influence of Aging on the Physical Mechanical Properties of Acrylic Resin Films Cast from Aqueous Dispersions and Organic Solutions. Drug Development and Industrial Pharmacy. 1993, vol. 19, No. 3 (315-332).
Gutierrez-Rocca J.S., McGinity J.W., Influence of Water Soluble and Insoluble Plasticizers on the Physical and Mechanical Properties of Acrylic Resin Copolymers, International Journal of Pharmaceutics, 1994, vol. 103, (293-301).
Obara S., McGinity J.W., Properties of Free Films Prepared from Aqueous Polymers by a Spraying Technique. Pharmaceutical Research. Jun. 1994, vol. 11 (15621567).
Wong D.Y.T., Waring M.J., Wright P., Aulton M.E., Elucidation of the Compressive Deformation Behavior of A-Lactose Monohydrate and Anhydrous A-Lactos Single Crystals by Mechanical Strength and Acoustic Emission Analyses. International Journal of Pharmaceutics. 1991, vol. 72 (233-241).
Waring M.J., Rubenstein M.H., Howard J.R., Acoustic Emission of Pharmaceutical Materials During Compression. International Journal of Pharmaceutics, 1987, vol. 36 (29-36).
Hakanen A., Laine E., Acoustic Emission During Powder Compaction and Its Frequency Spectral Analysis. Drug Development and Industrial Pharmacy, 1993, vol. 19 (2539-2560).
Hakanen A., Lairie E., Acoustic Characterization of a Micro-Crystalline Cellulose Powder During and After Its Compression. Drug Development and Industrial Pharmacy, 1995, vol. 21 (1573-1582).
Semis E., Camby-Perier L., Thomas G., Desfontaines M., Fantozzi G., Acoustic Emission of Pharmaceutical Powders during Compaction, Powder Technology, 2002, vol. 128, 2-3, (296-299).
Hardy L.J., Cook W.G., Predictive and Correlative Techniques for the Design, Optimization and Manufacture of Solid Dosage Forms, Journal of Pharmacy and Pharmacology, 2003 vol. 55 (1),3-18.
Morisseau K.M., Rhodes C.T., Near-Infrared Spectroscopy as a Nondestructive Alternative to Conventional Tablet Hardness Testing. Pharmaceutical Research, 1997, vol. 14 (1), 108-111.
Chen Y.X., Thosar S.S., Forbess R.A., Kemper M.S., Rubinovitz Shulda A.J., Prediction of Drug Content and Hardness of Intact Tablets Using Artificial Neural Network and Near-Infrared Spectroscopy, Drug Development and Industrial Pharmacy, 2001, vol. 27 (7), 623-631.
Donoso M., Kildsig D.O., Ghaly E.S., Prediction of Tablet Hardness and Porosity Using Near-Infrared Diffuse Reflectance Spectroscopy as a Nondestructive Method. Pharmaceutical Development and Technology, 2003, vol. 8 (4), 357-366.
Otsuka M., Yarnane I., Prediction of Tablet Hardness Based on Near Infrared Spectra of Raw Mixed Powders by Chemometrics, Journal of Pharmaceutical Sciences, Jul. 2006, vol. 95, No. 7 (1425-1433).
Saltelli A., Tarantola S., Campolongo F., Ratto M., Sensitivity Analysis in Practice, A Guide to Assessing Scientific Models, Joint Research Centre of the European Commission, John Wiley & Sons, Ltd. 2004, pp. 42-47.
Akseli I., Cetinkaya C., Air-coupled Non-contact Mechanical Property Determination of Drug Tablets. International Journal of Pharmaceutics. Mar. 2008, vol. 359 (25-34).
Akseli I., Cetinkaya C., Becker D., Ultrasonic Determination of Young's Moduli of the Coat and Core Materials of a Drug Tablet. International Journal of Pharmaceutical Sciences, 2009, vol. 370 (17-25).
Behneke H.H., Coating Thickness Measurement by the X-ray Fluorescence Method. Metal Finishing. 1984, vol. 82, No. 5 (33-39).
Cetinkaya C., Akseli I., Mani G.N., Libordi C.F., Varghese L., Non-Contact Mechanical Characterization and Testing of Drug Tablets, Advanced Ultrasonic Methods for Material and Structure Inspection, edited by T. Kundu, ISTE Science and Technical Publishing, UK, 2006, 319-369, Chapter 9.
Fitzgerald, A.J., Cule, B.E., Taday P.F., Nondestructive Analysis of Tablet Coating Thicknesses Using Terahetz Pulsed Imaging. Journal of Pharmaceutical Science, Jan. 1005, vol. 94 (No. 1), 177-183.
Mowery M.D., Sing R., Kirsch J., Razaghi A., Bechard S., Reed R.A., Rapid At-Line Analysis of Coating Thickness and Uniformity on Tablets Using Laser Induced Breakdown Spectroscopy, Journal of Pharmaceutical and Biomedical Analysis, 2002, vol. 28.
I. Varghese, L., Ban, M. D. M. Peri, C, Li, G. Subramanian, \and C. Detinkaya, Non-Contact Techniques for Drug Tablet Monitoring, PhramaPro, Oct. 4, 2005.
Ivin Varghese and Cetin Cetinkaya, Non-contact Photo-acoustic Defect Detection in Drug Tablets, submitted for publication in the Journal of Pharmaceutical Sciences., 2006.
Hancock, B.C., Colvin, J.T., Mullarney, M.P.Zinchuk, A.V., 2003. The relative densities of pharmaceutical powders, blends, dry granulations, and immediate-release tablets. Pharmaceutical Technology, 27, 64-80.
Kirsch J.D., Drennen J.K., 1999, Nondestructive tablet hardness testing by near-infrared spectroscopy: a new and robust spectral best-fit algorithm. Journal of Pharmaceutical and Biomedical Analysis, 19 (3-4), 351-362.

* cited by examiner

NON-CONTACT MECHANICAL PROPERTY DETERMINATION OF DRUG TABLETS

CROSS REFERENCE

This application is related to provisional application Ser. No. 60/783,574 filed on Mar. 20, 2006 entitled Method for Monitoring and Characterization of Solid Dosage during Compaction and Ser. No. 60/808,537 filed on May 26, 2006 entitled Method for Non-contact Mechanical Property Characterization and Monitoring of Drug Tablets and is hereby incorporated herein by reference.

FIELD OF INVENTION

This invention relates to real time testing of drug tablet mechanical properties, coat thickness and characterization using non-contact process pharmaceutical monitoring including acoustic process monitoring.

BACKGROUND OF INVENTION

In order to promote comprehensive quality assurance monitoring in the pharmaceutical industry the Food and Drug Administration (FDA) has initiated a program entitled the Process Analytical Technology (PAT) which is often defined as "a system for designing, analyzing, and controlling manufacturing through timely measurements (i.e. during processing) of critical quality and performance attributes of raw and in process materials, and processes with the goal of ensuring final pharmaceutical product quality." It is important to note that the term analytical in PAT is viewed broadly to include chemical, physical, microbiological, mathematical, and risk analysis conducted in an integrated manner. The approaches detailed in this disclosure are targeted for such monitoring and evaluation tasks.

Physical properties and mechanical integrity of drug tablets often affect their therapeutic functions. This disclosure presents non-contact/non-destructive techniques for determining the mechanical properties of coated tablets, such as Young's moduli, Poisson's ratios and mass densities as well as the thickness of the coating layer using an air-coupled approach is presented. Due to the elevated regulatory and competitive requirements, the demand for measuring and evaluating the mechanical properties of drug tablets has been increasing in the pharmaceuticals industry.

Compaction is a common production method for solid dosage formation from powder and/or granular materials in various industries. Solid dosage (e.g. drug tablets) cores are manufactured by applying pressure to a powder bed to compress the powder into a (porous) coherent/solid form. Compaction represents one of the most important unit operations in the pharmaceuticals industry. Physical and mechanical/elastic properties of the tablets, such as density, hardness and/or mechanical strength as well as geometric features, are determined during the compaction process. These properties can play crucial roles in pharmaceutical effectiveness and functions of a tablet such as tablet integrity and drug availability. The uniaxial compaction of a pharmaceutical powder results in an anisotropic and heterogeneous tablet with variations in such properties as density, porosity and mechanical strength throughout the tablet. During the compaction, various types of defect types can be created in tablets during compaction process, such as capping, chipping, cracking, and splitting. While many of these defect types can be easily identifiable through visual inspections of their exteriors, the defects formed in the interior of a tablet such as cracks are considerably more difficult to detect. Such invisible defects can result in functionally compromised tablets.

Some of the commonly defects occurred during compaction operation are as follows.

Capping is the term used, when the upper or lower segment of the tablet separates horizontally, either partially or completely from the main body of a tablet and comes off as a cap, during ejection from the tablet press, or during subsequent handling. Lamination is the separation of a tablet into two or more distinct horizontal layers. The main reason for these types of defect is that the air-entrapment in a compact during compression, and subsequent expansion of tablet on ejection of a tablet from a die causes capping and lamination.

Chipping is defined as the breaking of tablet edges, while the tablet leaves the press or during subsequent handling and coating operations. The major reasons of chipping include incorrect machine settings and specially mis-set ejection take-off.

Cracking (small, fine cracks) observed on the upper and lower central surface of tablets, or very rarely on the sidewall is often as a result of rapid expansion of tablets, especially when deep concave punches are used. Many mechanical and materials factors such as stress localization and poor adhesion conditions can cause cracks in a tablet core.

Cracking/Splitting is defect in which the film either cracks across the crown of the tablet (cracking) or splits around the edges of the tablet (Splitting) under internal stresses in the film that exceeds tensile strength of the film. Sticking refers to the tablet material adhering to the die wall. Filming is a slow form of sticking and is largely due to excess moisture in the granulation (due to improperly dried or improperly lubricated granules).

Picking is the term used when a small amount of material from a tablet is sticking to and being removed off from the tablet-surface by a punch face. Picking defect is more prevalent on the upper punch faces than on the lower ones. If tablets are repeatedly manufactured in this station of tooling, the size of the defect becomes larger the more and more material getting added to the already stuck material on the punch face. Picking is of particular concern when punch tips have engraving or embossing letters, as well as the granular material is improperly dried.

When the tablets adhere, seize or tear in the die, a film is formed in the die and ejection of tablet is hindered. This type of defect is termed as binding. With excessive binding, the tablet sides are cracked and it may crumble apart. Binding is usually due to excessive amount of moisture in granules, lack of lubrication and/or use of worn dies.

In recent years, deformation and compaction characteristics of the tableting materials have been intensely studied. See: Fell J. T., Newton, J. M., 1968, Tensile strength of lactose tablets, The Journal of Pharmacy and Pharmacology, 20, 657-659; Fell J. T., Newton, J. M., 1970, The prediction of the tensile strength of tablets, The Journal of Pharmacy and Pharmacology, 22, 247; Hancock, B. C., Colvin, J. T., Mullarney, M. P. Zinchuk, A. V., 2003, The relative densities of pharmaceutical powders, blends, dry granulations, and immediate-release tablets, Pharmaceutical Technology, 27, 64-80 (Payne et al.); R. S., Roberts R. J., Rowe R. C., McPartlin M., Bashall A., 1996, The mechanical properties of two forms of primidone predicted from their crystal structures, International Journal of Pharmaceutics, 145, 165-173 (Robert et al.); Roberts R. J., Payne R. S., Rowe R. C., 2000, Mechanical property predictions for polymorphs of sulphathiazole and carbamazepine, European Journal of Pharmaceutical Sciences, 9, 277-283; Roberts R. J., Rowe R. C., 1987, The Young's modulus of pharmaceutical materials, International Journal of Pharmaceutics, 37, 15-18; Bassam F., York P., Rowe R. C., Roberts R. J., 1990, Young's modulus of powders used as pharmaceutical excipients, International Journal of Pharmaceutics, 64, 55-60; and Rigdway K., Aulton M. E., 1970, The surface hardness of tablets, Journal of Pharmacy and Pharmacology, 22, 70-78, all hereby incorporated herein by reference.

One main objective has been to determine the powder behavior during compaction and to understand the effect of the processing of tableting stages on the compaction properties of final products. Even though physical-mechanical properties of tablets are known to influence the tablet chemical and physical stability, accuracy of dosage and appropriate self life, few studies have focused on properties such as the Young's modulus, tensile strength and Poisson's ratio of the core and coating layer of the tablets. See Felton L. A., Shah N. H., Zhang G., Infeld M. H., Malick A. W., McGinity J. W., 1996, Physical-mechanical properties of film-coated soft gelatin capsules, International Journal of Pharmaceutics, 127, 203-211 (Feltonet al.); and Stanley P., Rowe R. C. and Newton J. M., 1981, Theoretical considerations of the influence of polymer film coatings on the mechanical strength of tablets. Journal of Pharmacy and Pharmacology, 33, 557-560 both hereby incorporated by reference.

Fell and Newton as cited above investigated the tensile strength of the tablets by diametrical compression tests. Felton et al. as cited above studied the physical-mechanical properties of film-coated tablets including tensile strength, Young's modulus and tensile roughness using a diametrical compression test. In a diametrical compression test as discussed by Fell and Newton, the tablet is placed between two jaws and crushed. The force applied to break the tablet is recorded along with the outer dimensions of the tablet and tensile strength is calculated. The determination of the tensile strength of individual tablet components is used to predict the resultant tensile strength of tablet as a whole.

An important objective of the physical-mechanical property of coating films is to predict the stability and release property of film-coated dosage forms. Tablet coating has been effectively used to protect the dosage form from its environment, to control the release of active ingredients in the body, and to prevent interactions between ingredients. Additionally, tablet coating has improved the mechanical strength of the dosage form to preserve tablet integrity during packaging and shipping. Several researchers have focused on tensile strength and the elastic modulus of free-standing films prepared via aqueous coating technology. See Gutierrez-Rocca J. C. and McGinity J. W., 1993, Influence of aging on the physical-mechanical properties of acrylic resin films cast from aqueous dispersions and organic solutions, Drug Development and Industrial Pharmacy, 19, 315-332; Gutierrez-Rocca J. C. and McGinity J. W., 1994, Influence of water soluble and insoluble plasticizers on the physical and mechanical properties of acrylic resin copolymers, International Journal of Pharmaceutics, 103, 293-301; and Obara S, and McGinity J. W., 1994; Properties of free films prepared from aqueous polymers by a spraying technique; Pharmaceutical Research, 11, 1562-1567, all hereby incorporated by reference. The Obara and McGinty study cited above compared the properties of cast films to sprayed films. It has been reported that the mechanical property variation of the sprayed films are lower and their tensile strength are higher than those of the cast films.

Payne et al. and Roberts et al. (both cited above) developed a molecular modeling approach for predicting Young's moduli of compacts and tableting materials. A mechanical model of crystal structure was used to determine the crystal lattice energy, from which Young's moduli of a series of compacts prepared from aspirin and polymorphs of primidone, carbamazepine and sulphathiazole could be extracted. However, reportedly it is difficult to obtain the bulk elastic properties of tablet materials from the first principles based on molecular dynamic simulations.

Acoustic emission (AE) techniques during processes have been widely utilized in the pharmaceuticals industry due to its cost effective and noninvasive nature for monitoring granular materials to predict their flow, particle size and compaction properties of the final granules. Wong et al. differentiate the deformation mechanisms of single crystals of lactose monohydrate and anhydrous lactose by acoustic emission. It is reported that acoustic emission techniques can be employed to predict the compaction properties and brittleness of tableting materials if the bulk material is characterized by a single-crystal. See: Wong D. Y. T., Waring M. J., Wright P. and Aulton M. E., 1991, Elucidation of the compressive deformation behavior of $\alpha$-lactose monohydrate and anhydrous $\alpha$-lactose single crystals by mechanical strength and acoustic emission analyses, International Journal of Pharmaceutics, 72, 233-241 (Wong et al.) hereby incorporated by reference.

Waring et al. and Hakanen and Laine investigated the acoustic emission of lactose, sodium chloride, microcrystalline cellulose and paracetamol during compression using an acoustic transducer coupled to a portable activity meter. See Hakanen A., Laine E., 1993, Acoustic emission during powder compaction and its frequency spectral analysis, Drug Development and Industrial Pharmacy, 19, 2539-2560 (Waring et al.); and Hakanen A., Laine E., 1995, Acoustic Characterization of a micro-crystalline cellulose powder during and after its compression, Drug Development and Industrial Pharmacy, 21, 1573-1582, hereby incorporated by reference. By computationally analyzing the acoustic peaks related with the particle compression and decompression, it is concluded that the deformation mechanism and capping tendency can be predicted (See Hakanen and Laine cited above). Measuring acoustic emission from process chambers is also used for the identification of various phenomena that can occur during powder compaction of pharmaceutical products, such as granular rearrangement, fragmentation, visco-plastic deformation of grains or granules. See Serris E., Camby-Perier L., Thomas G., Desfontaines M., Fantozzi G., 2002. Acoustic Emission of Pharmaceutical Powders during Compaction, Powder Technology, 128, 2-3, 296-299. Acoustic emission is a passive acoustic technique thereby control over the nature of excitation is often limited.

Hardy and Cook reviewed the use of near infrared spectroscopy (NIR), a non-destructive remote technique as being primarily used for monitoring and predicting the end-points of granulation and drying operations. See Hardy I. J. and Cook W. G., 2003, Predictive and correlative techniques for the design, optimization and manufacture of solid dosage forms, Journal of Pharmacy and Pharmacology, 55 (1), 3-18 hereby incorporated by reference. The potential use of NIR has also been studied to predict tablet hardness. See Morisseau K. M., Rhodes C. T., 1997, Near-infrared spectroscopy as a nondestructive alternative to conventional tablet hardness testing, Pharmaceutical Research, 14 (1), 108-111; Kirsch J. D., Drennen J. K., 1999, Nondestructive tablet hardness testing by near-infrared spectroscopy: a new and robust spectral best-fit algorithm. Journal of Pharmaceutical and Biomedical Analysis, 19 (3-4), 351-362; Chen Y. X., Thosar S. S., Forbess R. A., Kemper M. S., Rubinovitz R. L., Shukla A. J., 2001, Prediction of drug content and hardness of intact tablets using artificial neural network and near-infrared spectroscopy, Drug Development and Industrial Pharmacy, 27 (7), 623-631;

Donoso M., Kildsig D. O., Ghaly E. S., 2003, Prediction of tablet hardness and porosity using near-infrared diffuse reflectance spectroscopy as a nondestructive method, Pharmaceutical Development and Technology, 8 (4), 357-366; Blanco M., Alcala M., 2006, Content uniformity and tablet hardness testing of intact pharmaceutical tablets by near infrared spectroscopy—A contribution to process analytical technologies, Analytica Chimica Acta, 557 (1-2): 353-359; and Otsuka M., Yamane I., 2006, Prediction of tablet hardness based on near infrared spectra of raw mixed powders by chemometrics, Journal of Pharmaceutical Sciences, 95, 1425-1433; all hereby incorporated by reference. However, its sensitive calibration and validation requirements for tablet hardness models remain a challenge since it is known that a slight variation in spectral peaks could invalidate a model.

Many solid pharmaceutical dosage mediums are produced with coatings, ideally the tablet should release the material gradually and the drug should be available for digestion beyond the stomach. Tablet coats serve a wide range of purposes, such as to control release of active ingredients in the body, to avoid irritation of oesophagus and stomach, and to protect the stomach from high concentrations of active ingredients, to improve drug effectiveness and stability and to regulate and/or extend dosing interval. In addition coats extend shelf life by protecting the ingredients from degradation, and to enhance the drug stability; that is to protect the drug from moisture, environmental gases, temperature variations and light, to provide a barrier to unpleasant taste or odor, and to improve appearance and acceptability as well as product identity (Cetinkaya et al., 2006; Mathiowitz, 1999). Coatings that form a controlling barrier to the release of the active ingredient and impart a sustained release of the drug are valuable delivery systems that provide convenience as well as patient compliance. Especially this is true for functional coatings such as an enteric coating which is designed to protect the tablet from the acidic environment of the stomach, resulting in drug release in the higher pH environment of the small intestine. Non-uniformity and/or surface or sub-surface defects of the tablet coating can compromise the desired dose delivery and bioavailability of the drug tablet as well as some other functions. Therefore, evaluating the properties of pharmaceutical coatings such as thickness and uniformity is important for demonstrating adequate process controls and quality and for ensuring optimal performance of the final product. As discussed above, in relation to quality and assurance, the Food and Drug Administration (FDA) has initiated a program entitled the Process Analytical Technology (PAT) to address various aspects of manufacturing problems in the pharmaceuticals industry. The PAT initiative is intended to improve consistency and predictability of drug action by improving quality and uniformity of pharmaceutical materials (Hussain et al., 2004).

In the pharmaceuticals industry, various techniques have been employed in coating thickness measurements such as ultrasonic measurements (Akseli et al., 2007), laser induced breakdown spectroscopy (LIBS) (Mowery et al., 2002), x-ray fluorescence method (Behncke, 1984), short pulsed of electromagnetic radiation (e.g. TeraHertz pulsed spectroscopy) (Fitzgerald et al., 2005), scanning thermal microscopy and Fourier transform infrared (FTIR) spectroscopy (Felton, 2003). In contact pulse-echo acoustic measurements, short ultrasonic pulses are generated by a piezoelectric transducer to transmit through the tablet. The ultrasonic pulse is reflected from the back side of the tablet and returned to the measurement surface via the shortest possible path. The reflected waveforms are captured by the same transducer and digitized in the oscilloscope. Measuring the displacement of the first back-wall echo from the start of the transmission peak, the longitudinal velocity of sound can be computed (Akseli et al., 2007). The thickness can then be calculated from the calibration of the time base. Throughout these measurements, coupling medium (water, grease, oil, and couplant gel) is required for facilitating the transmission of ultrasonic energy from the transducer into the test specimen.

Short pulsed of electromagnetic radiation and its reflections from interfaces (e.g. TeraHertz pulsed spectroscopy) is used for the analysis of coating thickness of tablets however due to its high cost it is difficult to use this technique in practice. Scanning thermal microscopy, laser induced breakdown spectroscopy (LIBS), x-ray fluorescence method and Fourier transform infrared (FTIR) spectroscopy are either expensive or unavailable for rapid on-line measurements for coating thicknesses of drug tablets. The proposed technique has potential to fulfill a major need in the analysis of drug delivery mechanisms.

Other relevant non-contact techniques for mechanical property determination adopted in various industrial applications include: (i) EMAT (Electro-Magnetic Acoustic Transducer)-based systems, (ii) optical methods, (iii) spectroscopy-based approaches (IR, near-IR, Raman scattering, Plasmon resonance). Nondestructive testing technologies based on EMATs are inapplicable to the determination of mechanical properties of tablets since tablet materials are typically not electrically conductive. Optical methods are often limited to surface, or near-surface properties, and are often irrelevant in sub-surface mechanical property analysis since, in general, drug tablets and coating layers are opaque in the visible and non-visible ranges. In tablet integrity applications, optical techniques are considered indirect methods for mechanical property monitoring and evaluation. For several years, spectroscopic techniques have been used in monitoring various process parameters such as moisture (water and/or alcohol levels) and blending properties of powders. In these measurements, surface properties are sufficient but the penetration of the electromagnetic waves inside the tablet is typically not required and/or not possible. There is no general method to predict the Young's modulus and Poisson's ratios of the core and coating layer of a tablet from the properties of its constituent components even if exact process steps are known. Non-contact acoustic techniques, detailed in this disclosure, have certain advantages in testing and evaluating the mechanical integrity of the core and the coating layer of drug tablets because of the ability for acoustic waves to penetrate the tablet surface and to vibrate entire tablet structures.

SUMMARY OF INVENTION

A first method of detecting, monitoring or characterizing a drug tablet during compaction includes: forming a tablet from a powder core in a compactor; transmitting acoustic waves into the powder core while the tablet is being formed; receiving acoustic waves from the powder core while the tablet is being formed; measuring data received from the received acoustic waves; calculating the data; and presenting the data. The acoustic waves are generated and received by transducers embedded in die and punches of the compactor. The instrumentation and signal processing are used for the measuring, calculating and presenting the data. The instrumentation includes a pulser/receiver unit, a digitizing oscilloscope, a computer and a computer program product. The computer program product is a computer usable medium having computer readable program code means embodied in the medium for detecting, monitoring or characterizing a drug tablet during compaction. The detecting, monitoring or characterizing includes transmitting acoustic waves into the powder core while the tablet is being formed; receiving acoustic waves from the powder core while the tablet is being formed; measuring data received from the received acoustic waves; calculating the data; and presenting the data.

The apparatus for detecting, monitoring or characterizing a drug tablet during compaction includes a compactor having a plurality of punches and die; a means for forming a tablet from a powder core; a plurality of transducers for transmitting acoustic waves into the powder core while the tablet is being formed; a plurality of transducers for receiving acoustic waves from the powder core while the tablet is being formed; instrumentation coupled to the transducers measuring, calculating and presenting the data. The transducers for transmitting acoustic signal waves to the powder core and the transducers for receiving acoustic waves from the powder core may be single transducer performing both functions.

Subsequent production decisions (e.g. rejection or continuation of the tablet in the manufacturing process) on the tablet can be made based on the processing of the acoustic signals. The main advantage of the invention is that it provides early warning on the mechanical and geometric state of a tablet during compaction to the operator before a number of other processing operations are applied.

A second method determines the mechanical characteristics and coating thickness of a tablet by exciting the tablet with an acoustic field. This followed with acquiring reflected signals from the tablet and digitizing the reflected signals. The mechanical characteristics are extracted from the digitized signals having resonance frequencies within a certain bandwidth. The exciting of the tablet includes vibrating the tablet. The acquiring of reflected signals includes detecting a shift of a reflected laser beam with an interferometer. The digititizing of the reflected signal is performed by an oscilloscope or a by a sampling board. The extracting of the mechanical characteristics from the digitized signals having resonance frequencies within a certain bandwidth is achieved using an iterative process. The iterative process is performed by a computer using a computer program product. The mechanical characteristics being measured include Young's modulus, Poisson's ratios, material mass densities and tablet coating thickness.

The computer program product is a computer usable medium having computer readable program code means embodied in the medium for determining the mechanical characteristics and coating thickness. Determining the mechanical characteristics and coating thickness includes exciting the tablet with an acoustic field; acquiring reflected signals from the tablet; digitizing the reflected signals; and extracting mechanical characteristics and coating thickness from the resonance frequencies within a certain bandwidth using an iterative process.

The apparatus for non-contact mechanical property characterization of drug tablets includes: a vacuum wand; an air coupled transducer; an inferometer; a vacuum control unit; pulse generating device; and measurement and calculation instrumentation. The vacuum control unit and vacuum wand retrieves and supports the tablets to be characterized. The air coupled transducer excites the tablets with acoustical waves. The inferometer measures a vibrational response from the excited tablets in a non-contact manner. The instrumentation digitizes and performs an iterative calculation of the vibrational responses to determine the mechanical characteristics of the tablet. The instrumentation further comprises a computer and a computer program product.

BRIEF DESCRIPTION OF DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

This application discloses methods of and devices for non-contact mechanical property determination and coat thicknesses of drug tablets.

A first method described in this disclosure is to detect, monitor and characterize a drug tablet during compaction by means of transmitting and receiving acoustic waves into the powder core, as it is formed in a press (compactor), via transducers embedded in the compactor die and punches. Subsequent production decisions (e.g. rejection or continuation of the tablet in the manufacturing process) on the tablet can be made based on the processing of the acoustic signals. The main advantage of this method is that it provides an early warning on the mechanical and geometric state of a tablet during compaction to the operator before a number of other processing operations are applied.

The objective of this method is to characterize and to monitor the mechanical (physical) and geometric state of the powder core in the die during compaction in a real-time manner. The characterization and detection/monitoring system consists of a plurality of transducers that generate and receive high frequency acoustic wave fields as well as electronic instrumentation and signal processing software.

Figure 1:
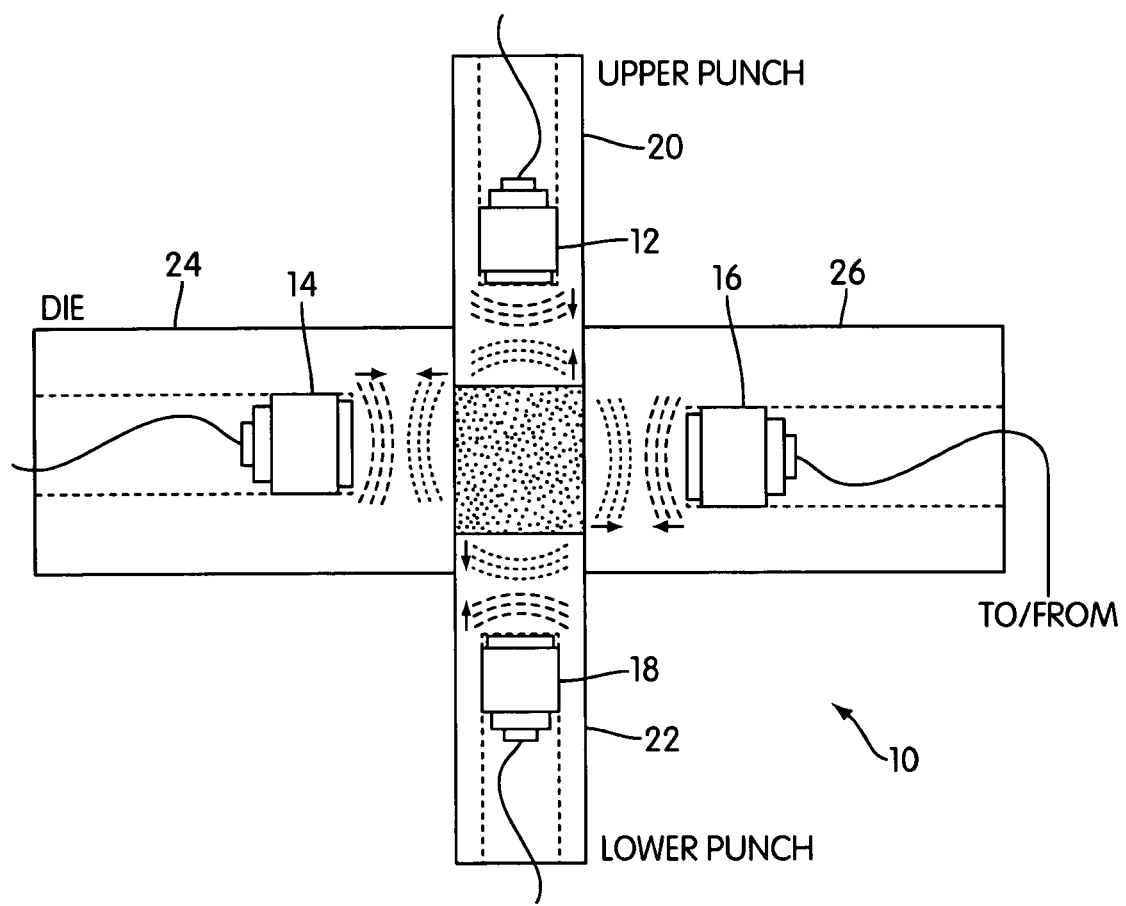
FIG. 1 illustrates four transducers embedded in the upper and lower punches of a compaction device and the die generate and detect acoustic waves through the power core during compaction.
Figure 2:
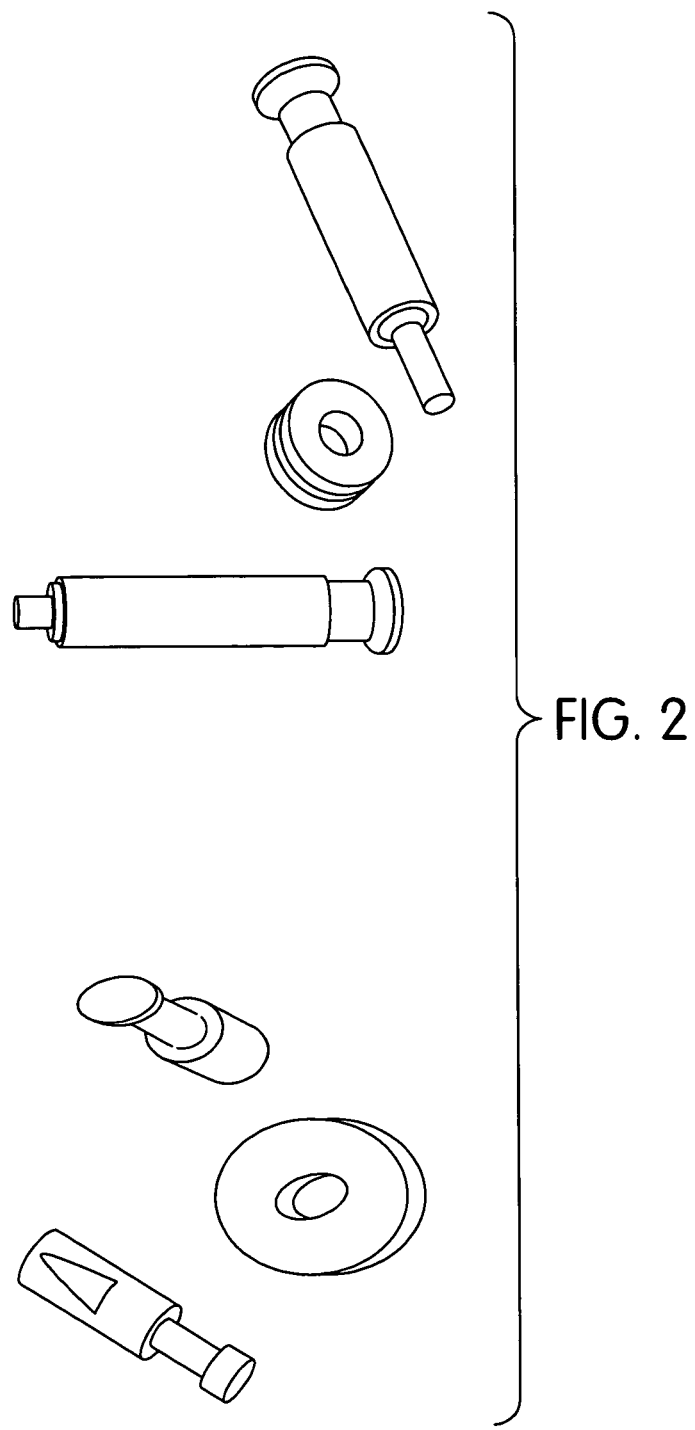
FIG. 2 illustrates examples of typical punches and die sets.

This method detects, monitors and characterizes a drug tablet during compaction by means of transmitting and receiving acoustic waves into the powder core, as it is formed in a press (compactor), via transducers embedded in the compactor die and punches as illustrated in FIG. 1. An image of a typical punches and die set is illustrated in FIG. 2.

FIG. 1 illustrates a compactions device 10 with four transducers embedded 12, 14, 16, and 18 embedded within an upper punch 20, a lower punch 22, a first die 24 and a second die 26. These transducers emit acoustic waves towards the punched tablet and measure its mechanical characteristic. These measurements are coupled to instrumentation calculate and present the results of these measurements. The propagation properties of the powder core in the die during compaction depend on the mechanical properties and their distributions as well as geometric factors (such as delamination zones and cracks). Therefore, by extracting these properties from the transmitted acoustic wave through the powder core, useful information about the material and geometric properties of the powder core can be obtained via instrumentation and signal processing.

Typical instrumentation in such a monitoring and characterization system consists of a pulser/receiver unit, a digitizing oscilloscope (or a sampling board) and a computer (Not shown). Signal processing software is needed to extract the acoustic wave properties of the powder core during compaction such as travel times, reflection and transmission coefficients, and dispersion curves. See references by Morse et al. and Krautkramer et al. cited below. A product of the method is a computer program product or an article of manufacture for use in a computer system having an operating system for use with an apparatus for detecting, monitoring or characterizing a drug tablet during compaction the computer program product having: a computer usable medium having computer readable program code means embodied in the medium for detecting, monitoring or characterizing a drug tablet during compaction, wherein the detecting, monitoring or characterizing includes transmitting acoustic waves into the powder core while the tablet is being formed; receiving acoustic waves from the powder core while the tablet is being formed; measuring data received from the received acoustic waves; calculating the data; and presenting the data.

Typical dwell times of the tablets in the die is on the order of a few milliseconds (ms) (1 ms=$10^{-3}$ second). For instance, the specified minimum and maximum dwell times for a Presster compaction simulator (Metropolitan Computing Corporation, NJ) are listed as 5.8 ms and 230 ms in the specification list for the Presster compaction simulator.

The travel time of an acoustic field in a tablet with typical dimensions (1-10 mm) is on the order of a few microseconds. Pulse repetition rates of pulser/receiver units can be as high as a few 10s of kHz. In other words, a commercially available pulser receiver unit can generate high frequency pulses with intervals as low as 0.1 ms (at a pulse repetition rate of 10 kHz). The time-scales of these two processes (e.g. ms for the compaction and μs for acoustic wave propagation) clearly indicate that the number of pulses transmitted and received in the powder core can be sufficiently high (on the order of 10) and the compaction process can be monitored via acoustic waves.

A second non-contact method described in this disclosure is to detect, monitor and characterize a drug tablet mechanical characteristics and coating thickness.

Set-Up and Configurations

Figure 3A:
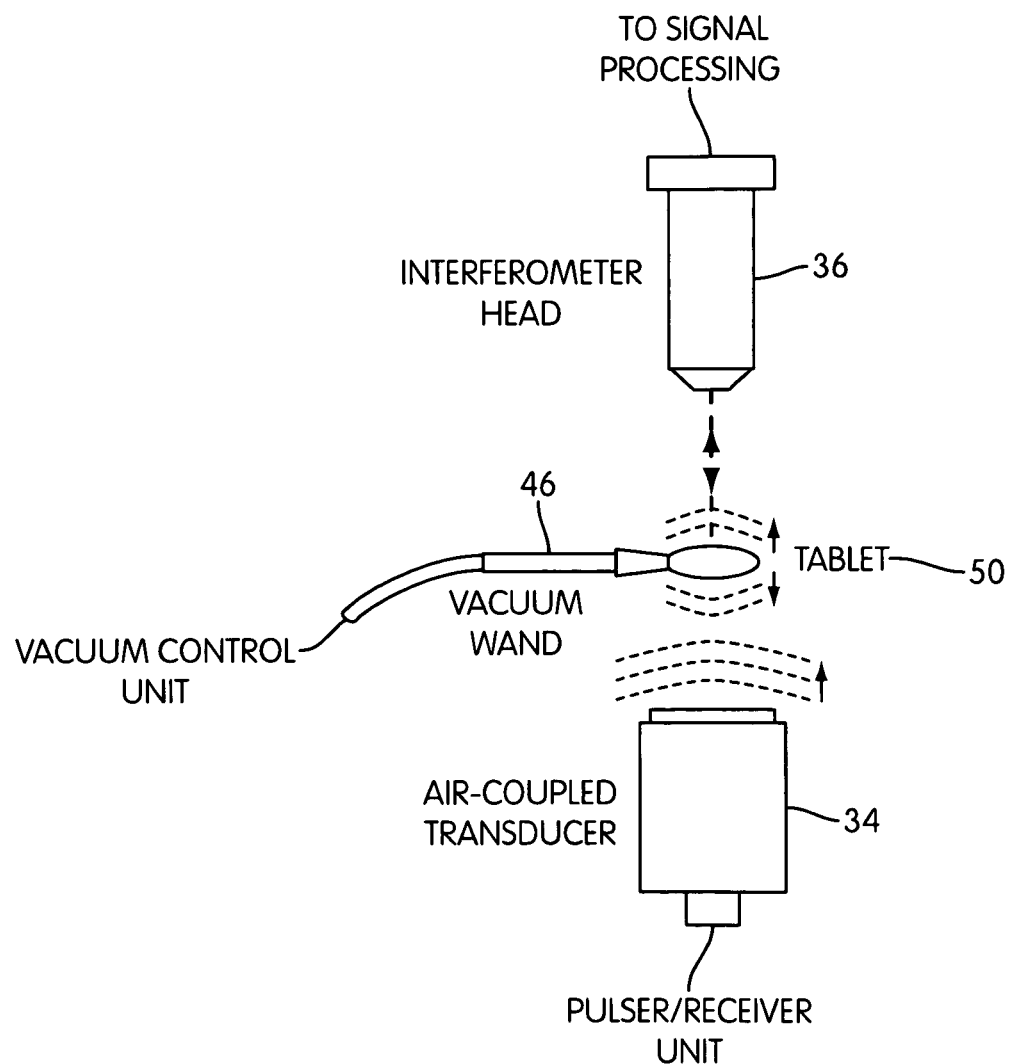
FIG. 3 illustrates schematics of a sample tablet mounting apparatus with the vacuum wand configuration (a) and the instrumentation diagram of the experimental setup (b)
Figure 3B:
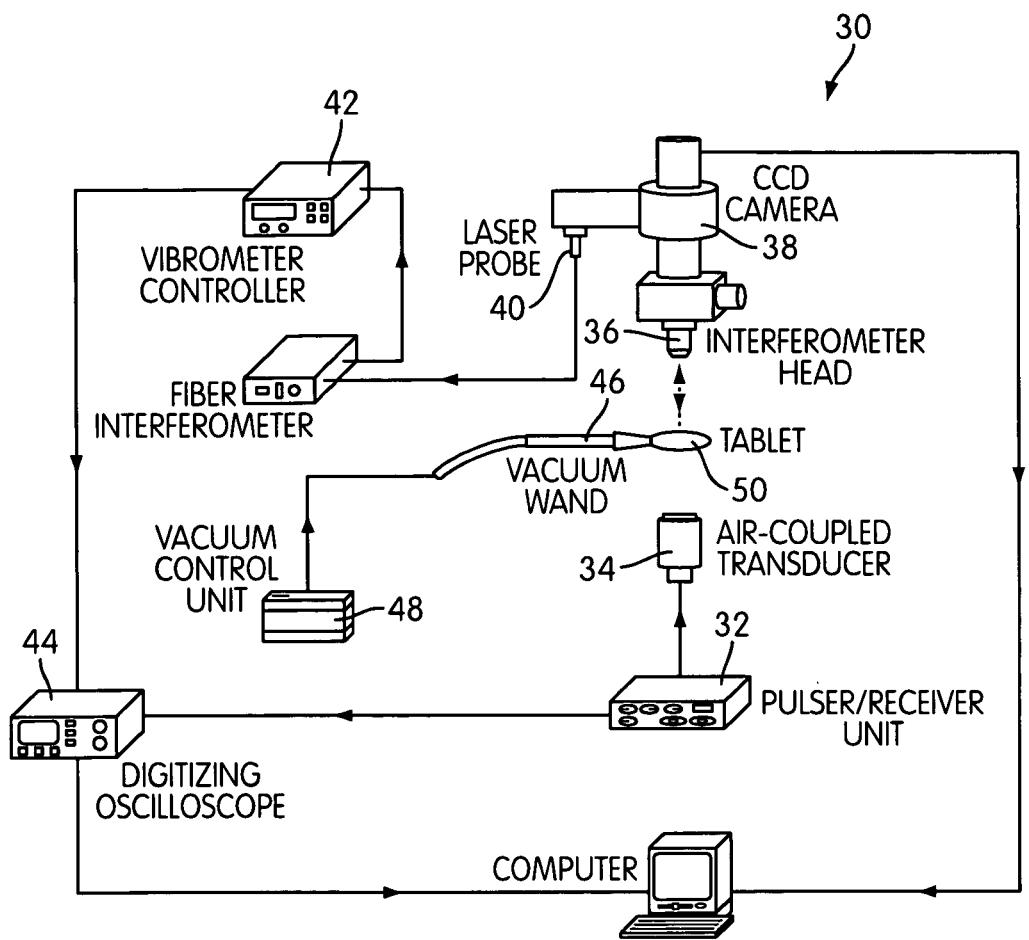
Figure 4A:
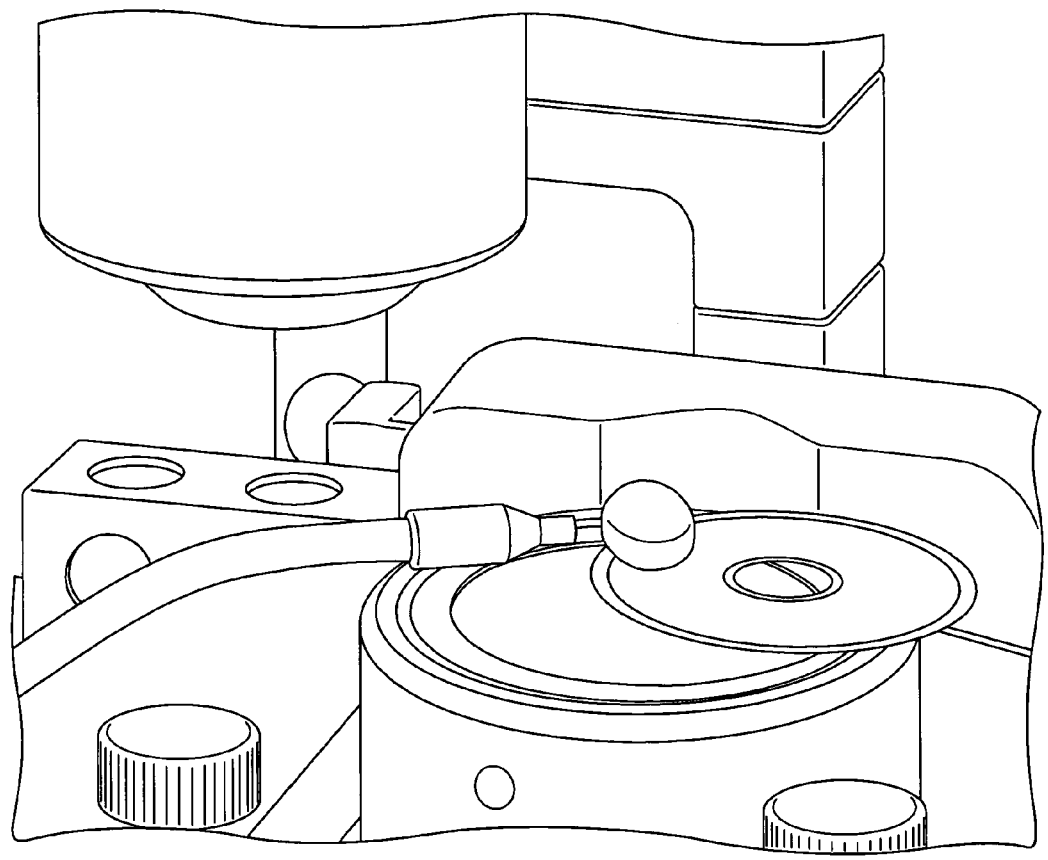
FIG. 4 illustrates images of the bottom excitation configuration using a 120 kHz transducer with a vacuum wand holding the tablet in place (a, b)
Figure 4B:
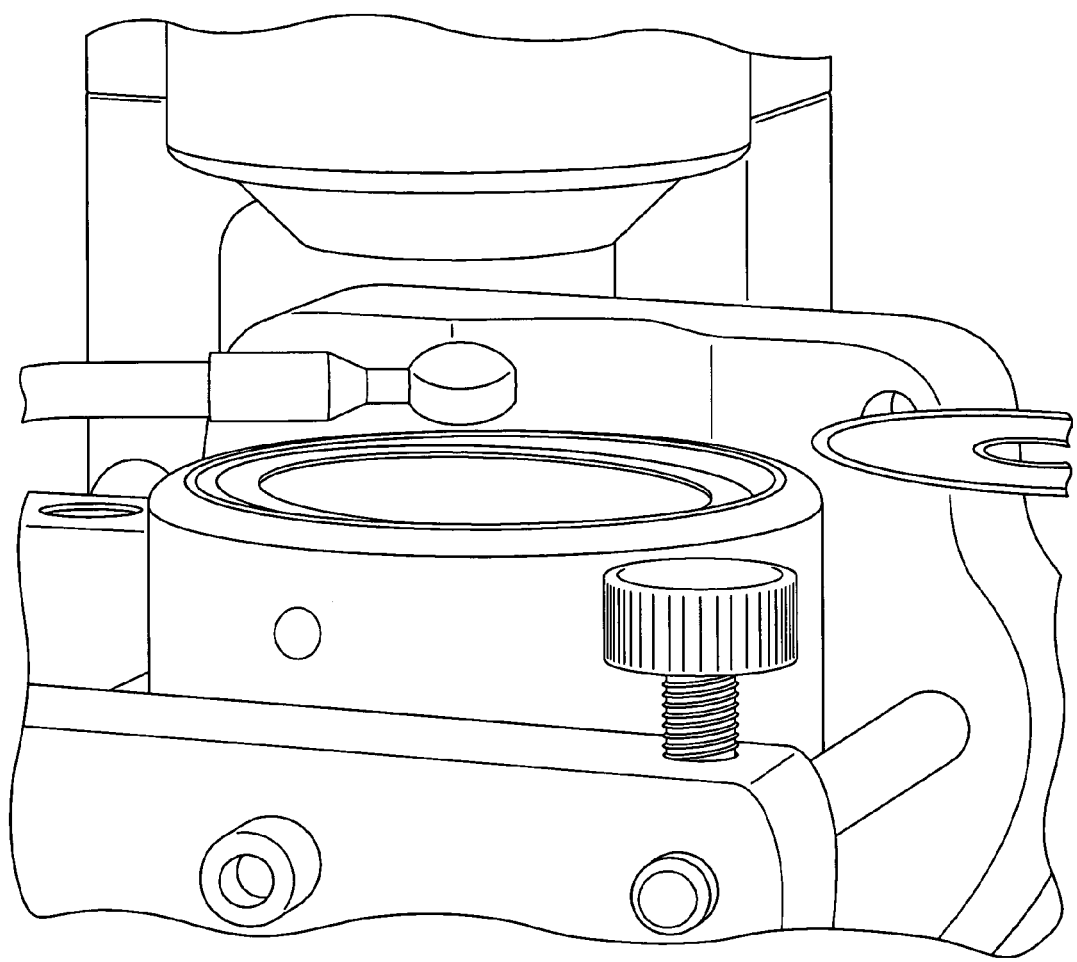

An experimental setup utilized for non-contact mechanical property determination of drug tablets is illustrated in FIG. 3 and FIG. 4. FIG. 3 (a) illustrates the tablet measuring portion on a non-contact system 10. A pulser/receiver unit 32 excites an air-coupled transducer 14 with a square pulse. The acoustic field generated on the active surface of the transducer 16 interacts with the tablet 50 and the tablet's vibrational modes are excited. A laser interferometer embedded within a microscope 44 measures the transient out-of-plane motion of a particular point on the surface of the vibrating tablet over a bandwidth of 20 kHz-30 MHz. The interferometer includes a displacement decoder (not shown) with sub-nanometer resolution in the range of ±75 nm The diameter of the interferometric laser beam is specified as small as a few micrometers so that high resolution scans are possible. The setup 30, as shown in FIG. 3(b) developed for the study incorporated a square pulser/receiver 32, an air-coupled transducer 34, a laser interferometer 36, a CCD camera 38, a laser probe 40 a vibrometer controller 42 and a digitizing oscilloscope 44 (or a sampling board, not shown), as well as a vacuum handling apparatus consisting of a vacuum wand 46 and a vacuum control unit 48 with a suction power of −30 kPa for holding a sample tablet 50.

Boundary conditions due to mounting techniques of a tablet have been found to play an important role in the accuracy and sensitivity of transient response measurements. An ideal tablet holding configuration must not interfere with the acoustic field exciting the vibrational motion of the tablet, while holding the tablet firmly with a minimal contact area. In an exemplary embodiment, a vacuum wand is utilized for holding the tablet. The main advantages of the vacuum wand include the firmness of grip, minimal contact surface area with the tablet, and rapidity of the handling apparatus. In experiments of the vacuum wand, a servo-motor controlled vacuum control unit is employed to automatically control suction power. As illustrated in FIGS. 4a and b, the vacuum wand is used to transport individual tablets from the tablet holding area to the test point.

Procedure for Determining Resonance Frequencies

Figure 5:
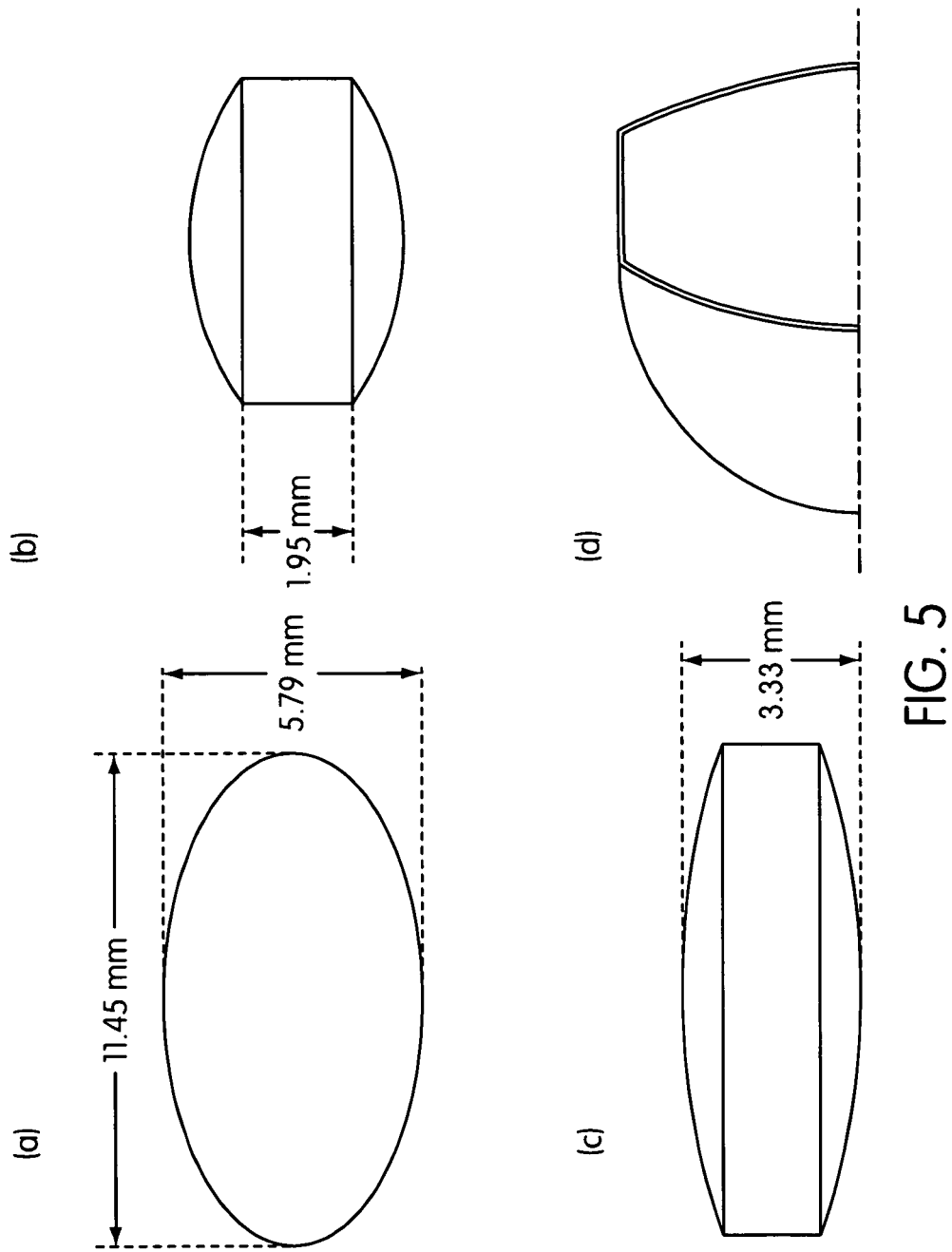
FIG. 5 illustrates the dimensions of a coated tablet with its top (a), front (b) and side (c) views.

Sample tablets with the average mass of 200 mg and with the characteristic dimensions of 5.79 mm width, 11.45 mm length, 3.33 mm thickness and a coating thickness of 102.3 μm were employed in the experimental apparatus as shown in FIG. 5. The method equally applies to tablets of different sizes. In determining the resonance frequencies of a sample tablet, the tablet is excited by an acoustic field generated by the air-coupled transducer 34. Since the bandwidth of the transducer overlaps with some of the resonance frequencies of the tablet, the propagating acoustic field generated by the air-coupled transducer excites a number of its vibrational modes. The tablet surface transient responses at measurement points are acquired by the interferometer in a non-contact manner by detecting the shift of a reflected laser beam and are digitized in the oscilloscope. In the vacuum wand mounting apparatus, the air-coupled transducer is placed under the sample tablet at the focal distance of the transducer (See FIG. 4). The focal distance of the transducer used was approximately 2.35 mm. The laser interferometer embedded into the optical microscope is directly focused at a point on the tablet surface through the objective lens of the microscope. The use of the microscope objective allows the laser probe beam to be focused at a spot that can be theoretically reduced to 0.5 μm using a 100× microscope objective. The sample tablet is placed under the objective at a distance of approximately 6.5 mm. The pulser/receiver 12 unit used in this embodiment delivers a 100V square pulse to the transmitting air-coupled transducer and provides a synchronizing pulse to trigger the digital oscilloscope (FIG. 3a). The acquired waveforms are digitized and averaged through the digital oscilloscope 38 and uploaded to a computer 44 in order to determine the vibrational resonance frequencies. Using an iterative computational procedure discussed below, the mechanical properties of the sample tablet core and coating layer can be extracted from a subset of the resonance frequencies in a certain bandwidth.

A computer program product is used with the computer for determining mechanical characteristics and coating thickness of a tablet the computer program product. The computer program product is a computer usable medium having computer readable program code means embodied in the medium for determining the mechanical characteristics and coating thickness and includes exciting the tablet with an acoustic field; acquiring reflected signals from the tablet; digitizing the reflected signals; extracting mechanical characteristics and coating thickness from the resonance frequencies within a certain bandwidth and performing an iterative process to determine the mechanical characteristics and coating thickness of the tablet.

Contact Measurements

Figure 6A:
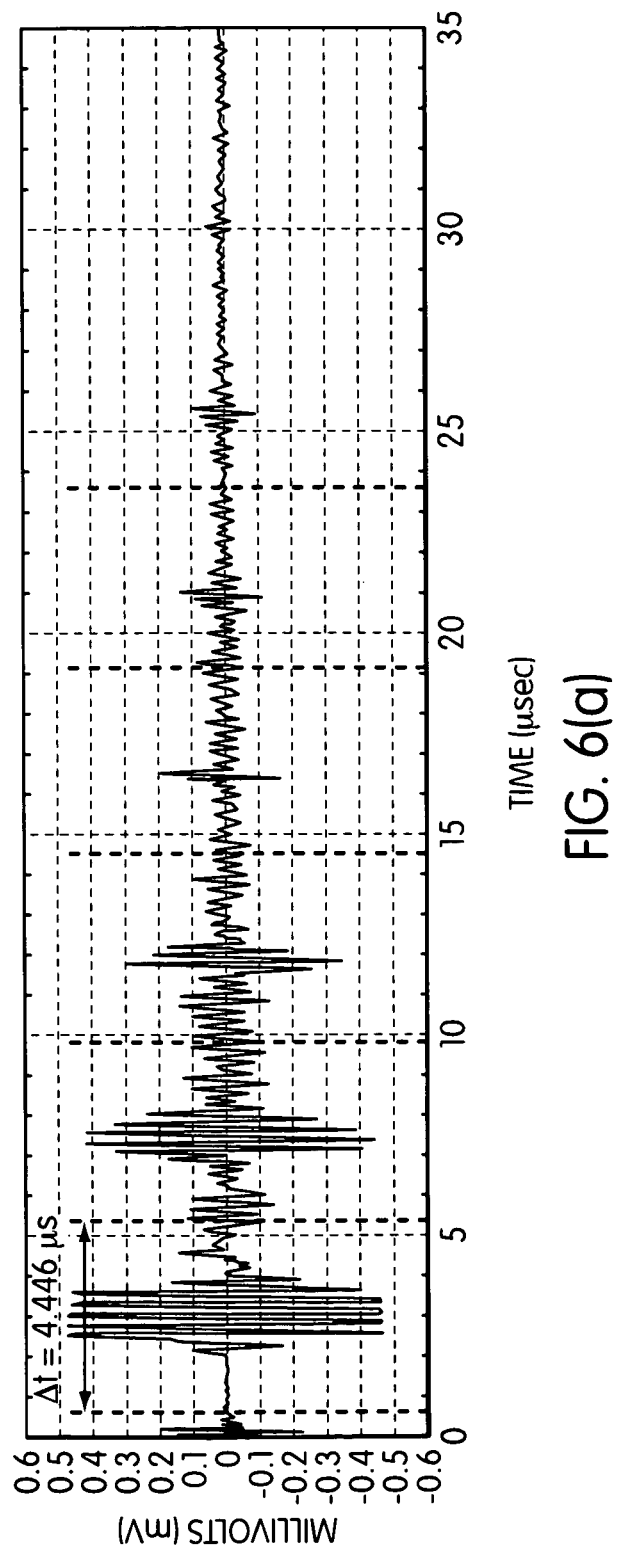
FIG. 6 illustrates waveforms indicating the time-of-flight and multiple reflections across the tablet cross-section for two different tablets (a, b) in the pulse-echo mode.
Figure 6B:
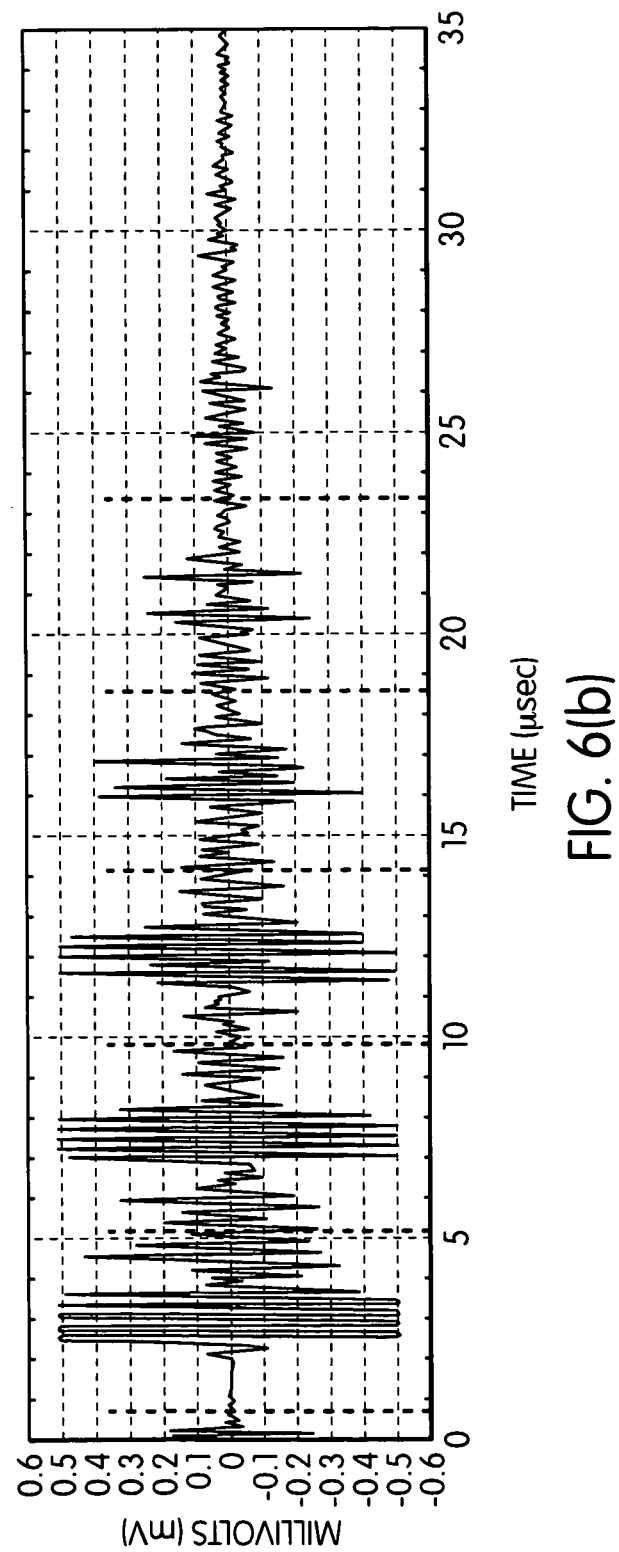

For verification purposes, the Young's modulus of a sample tablet core ($E_{core}$) is obtained using contact time-of-flight ultrasonic measurements. The mass densities of the core ($P_{core}$) and the coating material ($\rho_{coat}$) of the sample tablet are calculated from direct mass measurements of tablets with various coating thicknesses for known tablet geometry. Property predictions based on contact measurements are used for determining initial mechanical properties and for confirming (non-contact) experimentally obtained mechanical properties. In determining the Young's modulus of the core material ($E_{core}$) of the sample tablet, a direct measurement ultrasonic method (pulse-echo mode) is employed. In this test, short ultrasonic pulses are generated by a piezoelectric transducer with a central frequency to transmit through the tablet. The ultrasonic pulse is reflected from the back side of the tablet and returned to the measurement surface via the shortest possible path. The reflected waveforms are captured by the same transducer and digitized in the oscilloscope, as illustrated in FIG. 6. The thickness of the tablet can easily be measured precisely. The time of flight of an acoustic pulse is a function of its thickness and mass density as well as the tablet's Young's modulus. The longitudinal velocity of sound $c_L$ and Young's modulus of the core material of the tablet are easily computed. Consistent waveforms providing the time-of-flight across the tablet thickness for two different tablets are depicted in FIGS. 4a and b. The computed Young's modulus of the core of the sample tablet ($E_{core}$=2628.92 MPa) is included in Table 1. Table 1 outlines the relationships of the various properties used in the iterative computational procedure. $\bar{p}^*$ is the vector of starting mechanical property for the iterative computational procedure. $\bar{p}_1^e$, $\bar{p}_2^e$, $\bar{p}_3^e$ are the extracted mechanical property vectors upon completion of iterative procedure for $\bar{p}^*$ for Tablet 1, Tablet 2, Tablet 3, respectively. $\bar{p}^c$ is the measured and estimated mechanical property vector; $E_{core}$ is calculated from the contact measurements, $\rho_{core}$ and $\rho_{coat}$ are calculated from direct mass measurements. Percentage convergences of initial and experimental mechanical property vectors are shown for three tablets. The estimated mechanical properties ($V_{core}$, $E_{coat}$, $V_{coat}$) for $\bar{p}^c$ are indicated by an asterix.

TABLE 1

| Mechanical Properties | $\bar{p}^*$ | $\bar{p}_1^e$ | $\bar{p}_2^e$ | $\bar{p}_3^e$ | $\bar{p}^c$ | Convergence (%): $\bar{p}^* - \bar{p}_i^e$ | | |
|---|---|---|---|---|---|---|---|---|
| | | | | | | Tablet 1 | Tablet 2 | Tablet 3 |
| $E_{core}$ (MPa) | 3154.704 | 2648.220 | 2691.112 | 2666.287 | 2628.920† | 19.125 | 17.227 | 18.318 |
| $\rho_{core}$ (kg/m³) | 1591.548 | 1335.763 | 1348.758 | 1329.848 | 1326.290† | 19.207 | 18.001 | 19.679 |
| $v_{core}$ | 0.388 | 0.330 | 0.331 | 0.330 | 0.330* | 17.575 | 17.185 | 17.576 |
| $E_{coat}$ (MPa) | 3600.000 | 3023.150 | 3041.635 | 3038.521 | 3000* | 19.081 | 18.357 | 18.478 |
| $\rho_{coat}$ (kg/m³) | 868.410 | 730.730 | 737.883 | 729.761 | 723.675† | 18.841 | 17.689 | 18.999 |
| $v_{coat}$ | 0.447 | 0.382 | 0.385 | 0.381 | 0.380* | 17.015 | 16.104 | 17.292 |

Finite Element Study for Tablet Spectral Properties

The spectral properties of a tablet are related to its mechanical properties (e.g. Young's moduli ($E_{core}$, $E_{coat}$), Poisson's ratios ($v_{core}$, $v_{coat}$) and material mass densities ($\rho_{core}$, $\rho_{coat}$) of the core and the coating layer) as well as its geometry (e.g. shape and dimensions of the core and the coating layer). Using a finite element algorithm, such as the Lanczos method, the spectral properties of the tablet (e.g. a set of resonance frequencies and corresponding mode shapes) can be obtained provided that the mechanical properties and geometry of the tablet are available. However, the extraction of the tablet mechanical properties from its measured resonance frequencies requires the use of an iterative computational procedure such as Newton's method as well as a method to compute its resonance frequencies.

In the finite element study employed to compute natural frequencies of the tablets, a three-dimensional mesh for the tablet is modeled as homogenous and isotropic elastic solid consisting of a core and a coating layer for numerical predictions of the tablet resonance frequencies. The top, front and side views illustrating outer dimensions and cross-sectional area of the coated sample tablet with a coating thickness of 120.3 μm used in the finite element analysis are depicted in FIG. 3. Four-node linear tetrahedron elements are used in the mesh generation for the coated tablet. The number of elements, number of nodes, degrees of freedom and element size of the meshed coated tablet are 62,635, 14,357, 43,071, and 250 μm, respectively. The Lanczos eigenvalue solver implemented in the commercial software package ABAQUS is employed to obtain the resonance frequencies of the modeled tablet in the frequency range of 40 kHz to 200 kHz for given material properties.

Experimental Resonance Frequency Measurements

Figure 7A:
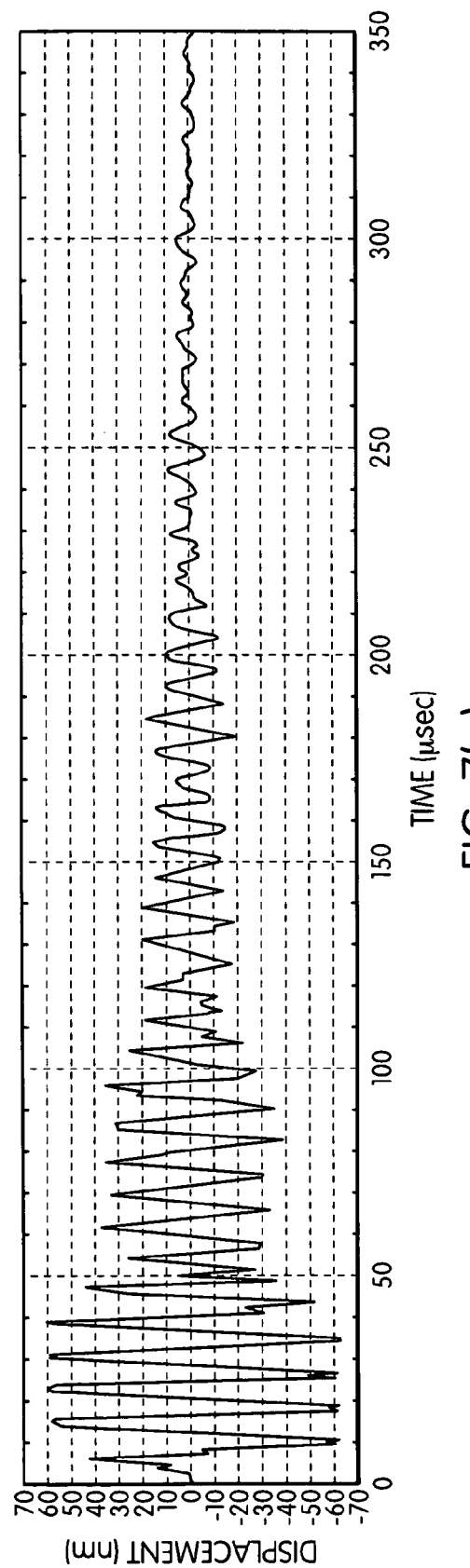
FIG. 7 illustrates the transient displacement (a) and the frequency response (b) of a spot on the active surface of the transducer under a square pulse excitation.
Figure 7B:
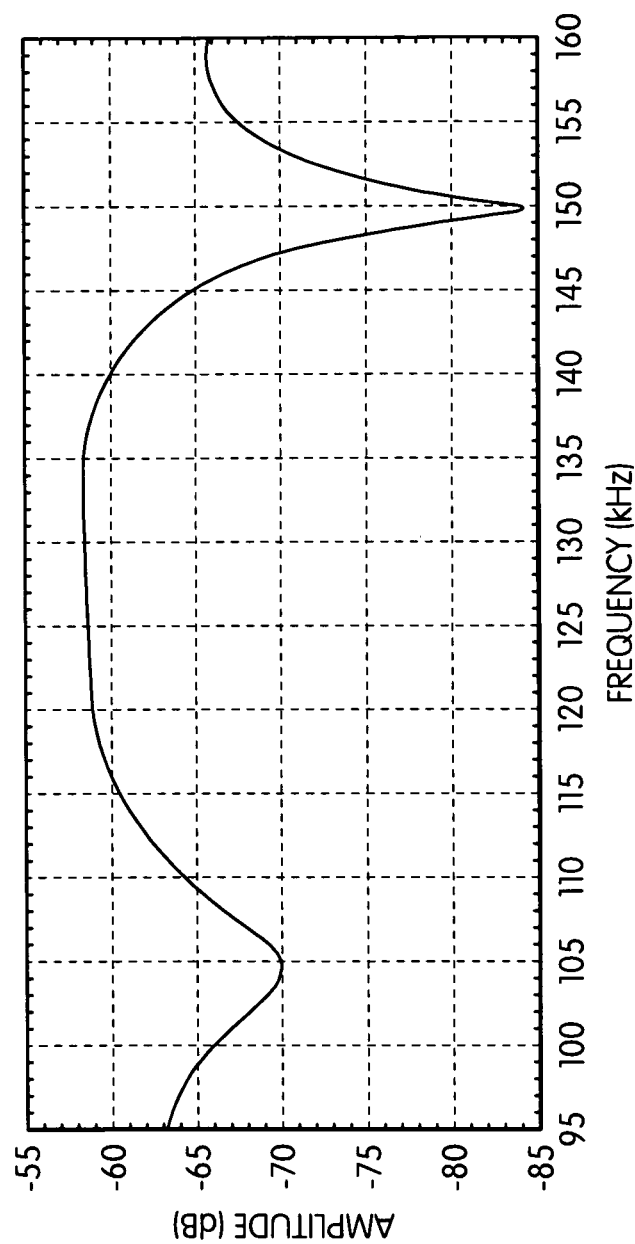
Figure 8A:
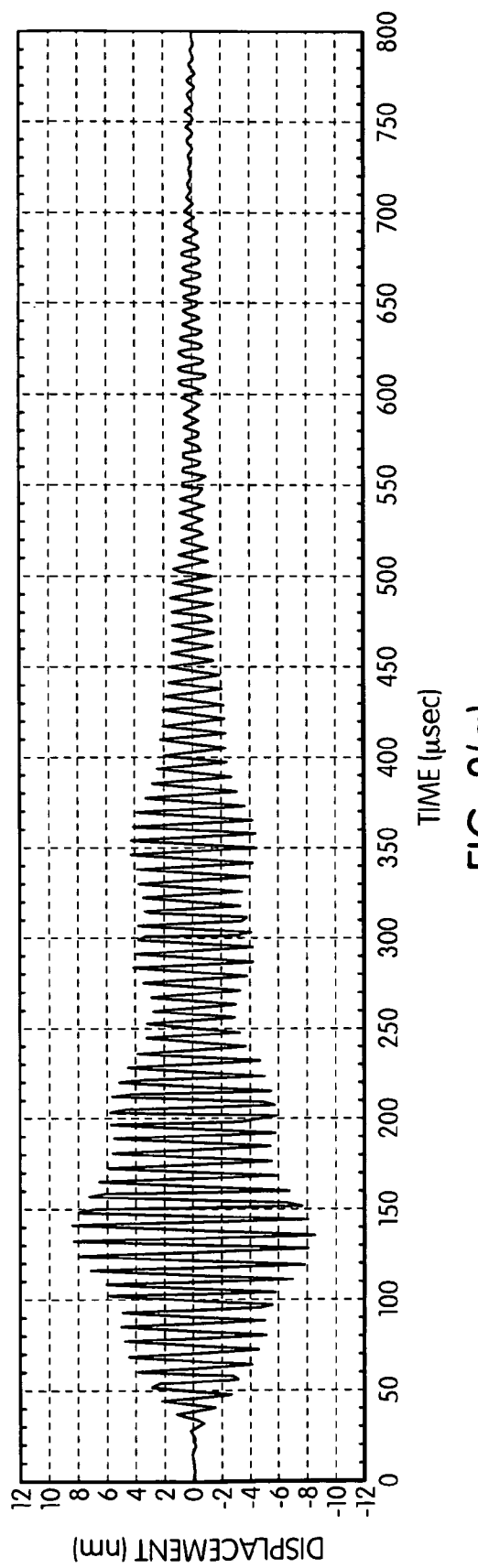
FIG. 8 illustrates, the waveforms of two tablets held with the vacuum wand (a, b,) and comparison of their frequency responses (c)
Figure 8B:
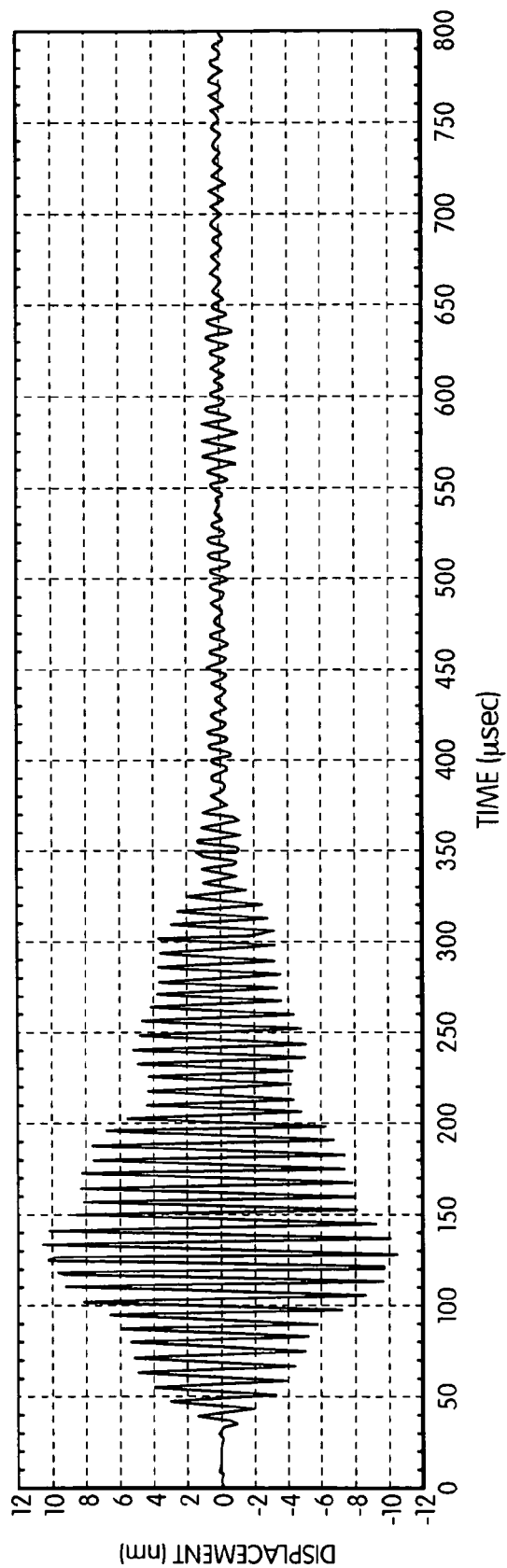
Figure 8C:
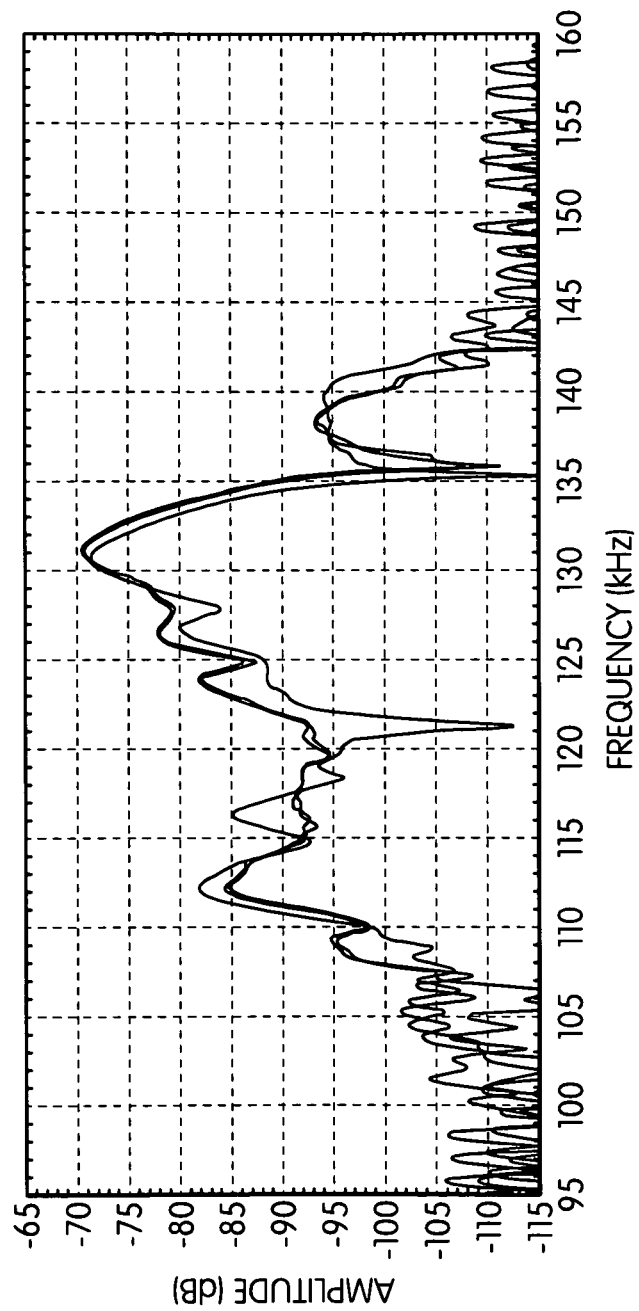

Resonance frequencies of the tablet are obtained by applying the Fast Fourier Transform (FFT) algorithm on the acquired waveforms under air-coupled excitation. The frequency range of the measurements is limited to 105 kHz because 150 kHz due to the bandwidth of the transducer employed in the experiments (See FIG. 7). In the experiments conducted with the vacuum wand, the resonance frequencies and the displacement of the tablet are clearly apparent. The transient surface displacement responses and frequency responses for three sample tablets were measured utilizing the vacuum wand mounting apparatus (FIG. 8). Consistent waveforms obtained over an extended time period in the experiments indicate that the air-coupled excitation and the experimental set-up are repeatable and stable.

Sensitivity Analysis for Extracting Tablet Mechanical Properties

In order to extract the mechanical property parameters ($E_{core}$, $E_{coat}$, $v_{core}$, $v_{coat}$, $\rho_{core}$, $\rho_{coat}$) of sample tablets from their resonance frequencies, an iterative procedure based on Newton's method is adopted. From a finite element study, it is observed that shifts in resonance frequencies are nearly linear with the reasonable changes in the mechanical properties, and no intersection of modes is realized within ±20% variation of the initial (estimate) mechanical properties. If modes traverse, the corresponding resonance frequencies will not coincide with their ordered mode shapes and all mode shapes and related resonance frequencies must be verified before continuing the inversion process.

The sensitivity analysis is based on the assumption that there is a well-defined relationship between a change in certain parameters of interest and other parameters of interest. In this type of analysis for mechanical properties, a series of either numerical or actual tests are conducted in which the (mechanical) parameters are altered to approximate these relationships between changes in the (mechanical) parameters, and corresponding changes in the natural frequencies. The result of such a study is sensitivity coefficients that can be used to approximate the assumed relationship. From these sensitivity coefficients, the actual mechanical properties can approximately be extracted within ranges of parameters.

In the mechanical property extraction, a set of initial (estimate) mechanical property vector is chosen $\bar{p}_k^*$ (Table 1) and the corresponding resonance frequency vector $\bar{f}_k^*$ is calculated via the method (Table 2) and each iteration step is denoted by index k. Each mechanical property parameter ($E_{core}$, $\rho_{core}$, $v_{core}$, $E_{coat}$, $\rho_{coat}$, $v_{coat}$) and mode numbers obtained from finite element are denoted by indices i and j, respectively. The thickness of the coat can also be added to this vector when the coat thickness is to be determined. Consistent six modes calculated from finite element (j=1, 2, ... 6) for $\bar{p}_k^*$ compared to experimentally obtained resonance frequencies $\bar{f}_{v_1}^e$, $\bar{f}_{v_2}^e$, $\bar{f}_{v_3}^e$ (Table 2) for the three sample tablets selected for sensitivity calculations. The i-th component of $\bar{p}_k^*$ is perturbed by a factor of (1+e) and the six resulting perturbed material property vectors are denoted by $\bar{p}_i$ (i=1, 2, ..., 6). The finite element model is run for each $\bar{p}_i$ to determine the corresponding six resonance frequency vectors $\bar{f}_i'$ and their shifts $\Delta\bar{f}_i = \bar{f}_i' - \bar{f}_i^*$. Using the first term in Taylor's expansion, the sensitivity coefficient vector $\{s\}$ is approximated for i=1, 2, ..., 6 as:

$$\Delta \bar{f}_i \cong \{s\}^T \cdot \{\Delta p\} \quad (1)$$

where $$\{\Delta p\} = \{\Delta E_{core} \; \Delta\rho_{core} \; \Delta v_{core} \; \Delta E_{coat} \; \Delta\rho_{coat} \; \Delta v_{coat}\}^T$$

$$\{s\} = \left\{\frac{\partial f_j}{\partial E_{core}} \; \frac{\partial f_j}{\partial \rho_{core}} \; \frac{\partial f_j}{\partial v_{core}} \; \frac{\partial f_j}{\partial E_{coat}} \; \frac{\partial f_j}{\partial \rho_{coat}} \; \frac{\partial f_j}{\partial v_{coat}}\right\}^T$$

j is the mode number, $\Delta \bar{p} = \bar{p}_i - \bar{p}^*$, $\{s\}$ the sensitivity coefficient vector and $\Delta \bar{f}_i = \bar{f}_i' - \bar{f}_i^*$. After running the finite element model and applying [Eq.1] for i=1, 2, ..., 6 to calculate the sensitivity coefficients for j=1, 2, ..., 6, (j=7 is needed if the thickness of the tablet is needed) the sensitivity tangent matrix $[S_\epsilon]_k$ is constructed for the selected six mode:

$$[S_\epsilon]_k = \begin{bmatrix} \frac{\partial f_1}{\partial E_{core}} & \frac{\partial f_1}{\partial \rho_{core}} & \frac{\partial f_1}{\partial v_{core}} & \frac{\partial f_1}{\partial E_{coat}} & \frac{\partial f_1}{\partial \rho_{coat}} & \frac{\partial f_1}{\partial v_{coat}} \\ \frac{\partial f_2}{\partial E_{core}} & \frac{\partial f_2}{\partial \rho_{core}} & \frac{\partial f_2}{\partial v_{core}} & \frac{\partial f_2}{\partial E_{coat}} & \frac{\partial f_2}{\partial \rho_{coat}} & \frac{\partial f_2}{\partial v_{coat}} \\ \frac{\partial f_3}{\partial E_{core}} & \frac{\partial f_3}{\partial \rho_{core}} & \frac{\partial f_3}{\partial v_{core}} & \frac{\partial f_3}{\partial E_{coat}} & \frac{\partial f_3}{\partial \rho_{coat}} & \frac{\partial f_3}{\partial v_{coat}} \\ \frac{\partial f_4}{\partial E_{core}} & \frac{\partial f_4}{\partial \rho_{core}} & \frac{\partial f_4}{\partial v_{core}} & \frac{\partial f_4}{\partial E_{coat}} & \frac{\partial f_4}{\partial \rho_{coat}} & \frac{\partial f_4}{\partial v_{coat}} \\ \frac{\partial f_5}{\partial E_{core}} & \frac{\partial f_5}{\partial \rho_{core}} & \frac{\partial f_5}{\partial v_{core}} & \frac{\partial f_5}{\partial E_{coat}} & \frac{\partial f_5}{\partial \rho_{coat}} & \frac{\partial f_5}{\partial v_{coat}} \\ \frac{\partial f_6}{\partial E_{core}} & \frac{\partial f_6}{\partial \rho_{core}} & \frac{\partial f_6}{\partial v_{core}} & \frac{\partial f_6}{\partial E_{coat}} & \frac{\partial f_6}{\partial \rho_{coat}} & \frac{\partial f_6}{\partial v_{coat}} \end{bmatrix}$$

Using $[S_\epsilon]_k$, the change in mechanical properties vector due to a shift $\{\Delta \bar{f}_k\}$ in the selected set of resonance frequencies can be approximated by $$\{\Delta \bar{p}\}_k = [S_\epsilon]_k^{-1} \cdot \{\Delta \bar{f}_k\} \quad (2)$$

where $\Delta \bar{f}_k = \bar{f}_v^e - \bar{f}_k^*$, and $\{\Delta \bar{p}\}_k$ the change in mechanical properties after the completion of an iteration with the perturbation $\bar{p}_k^e = \bar{p}_k^* + \Delta \bar{p}_k$ (see Table 1 for their numerical values). In this study, a number of iterations are executed to approximate values for $_{core}$, $_{coat}$, $_{core}$, $_{coat}$, $_{core}$ and $_{coat}$. Once singularity is observed in the tangent matrix $[S_\epsilon]_k$ or $\{\Delta \bar{p}\}_k$ values converge to zero the iteration loop is terminated. The values of $\bar{p}^*$ used in the last iteration correspond to the experimental mechanical property vector $\bar{p}_k^e$ of the core and coating of the tablet since $\Delta \bar{p}_k \cong 0$ (see Table 1 for the numerical values for the three sample tablets).

Figure 11:
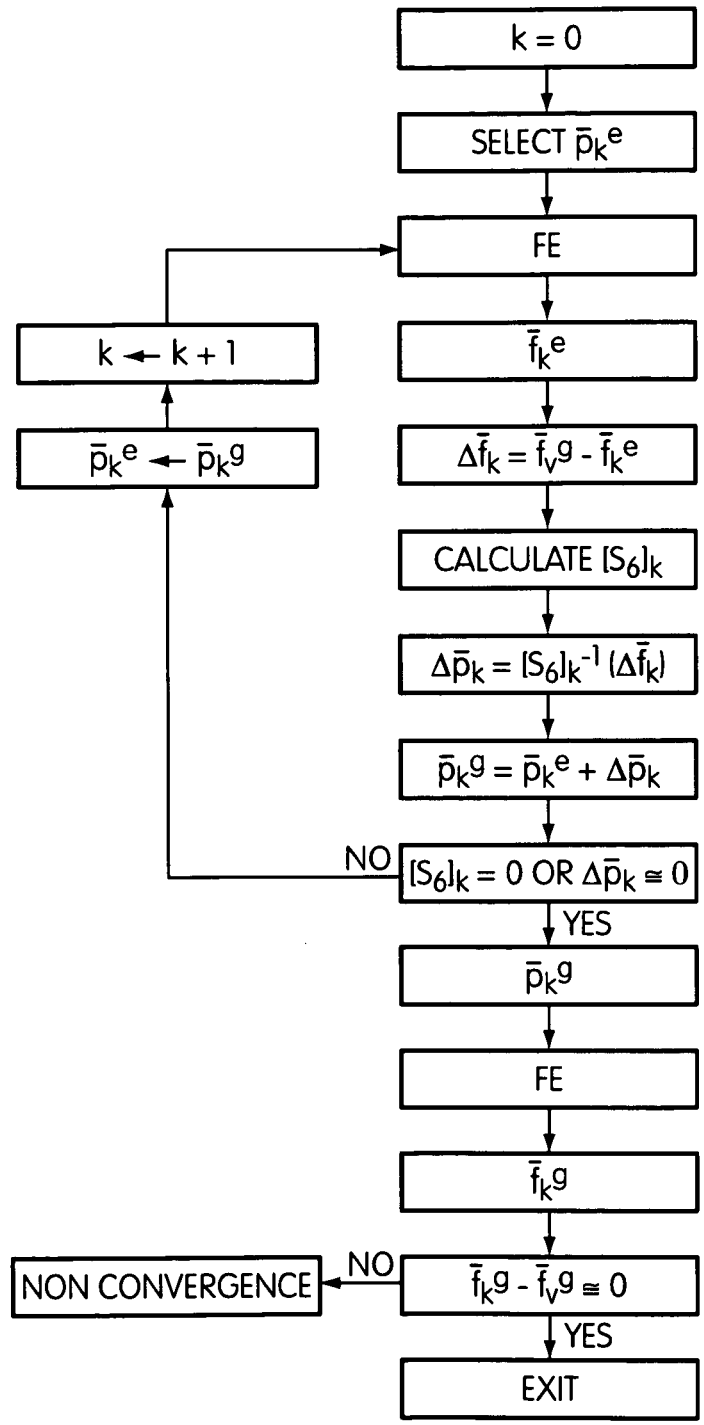
FIG. 11 illustrates a flow chart for the iterative process.

A flow chart for this iterative process is depicted in FIG. 11.

After extracting the mechanical properties for each tablet, the finite element method is employed to determine the corresponding resonance frequencies $\bar{f}_1^e$, $\bar{f}_2^e$, $\bar{f}_3^e$ for comparison purposes (see Table 2 for their numerical values). Due to tablet to tablet variations, small differences are detected in mechanical properties and resonance frequencies among three sample tablets. Within ±20% variations of the mechanical properties, changes in resonance frequencies are calculated approximately in the range of ±1.5% as listed in Table 1 and Table 2. The percent error between the experimental resonance frequencies ($\bar{f}_{v_1}^e$, $\bar{f}_{v_2}^e$, $\bar{f}_{v_3}^e$) and the finite element resonance frequencies ($\bar{f}_1^e$, $\bar{f}_2^e$, $\bar{f}_3^e$) corresponding to extracted mechanical properties is within ±1.5% for three sample tablets (Table 2).

TABLE 2

| | | | | | Convergence (%): $\bar{f}^* - \bar{f}_i^e$ | | |
|---|---|---|---|---|---|---|---|
| Modes | $\bar{f}^*$ | $\bar{f}_1^e$ | $\bar{f}_2^e$ | $\bar{f}_3^e$ | Tablet 1 | Tablet 2 | Tablet 3 |
| 8 | 107,331 | 109,135 | 109,338 | 109,675 | −1.653 | −1.835 | −2.137 |
| 9 | 112,089 | 112,175 | 113,391 | 113,750 | −0.076 | −1.148 | −1.460 |
| 11 | 120,891 | 122,621 | 122,869 | 123,235 | −1.411 | −1.609 | −1.902 |
| 13 | 122,150 | 123,863 | 124,118 | 124,492 | −1.383 | −1.585 | −1.881 |
| 14 | 131,641 | 131,646 | 133,017 | 133,362 | −0.004 | −1.034 | −1.290 |
| 15 | 136,547 | 138,418 | 138,776 | 138,157 | −1.352 | −1.606 | −1.165 |

TABLE 2

| | | | | | Error (%): $\bar{f}^c - \bar{f}_{v_i}^e$ | | |
|---|---|---|---|---|---|---|---|
| Modes | $\bar{f}^c$ | $\bar{f}_{v_1}^e$ | $\bar{f}_{v_2}^e$ | $\bar{f}_{v_3}^e$ | Tablet 1 | Tablet 2 | Tablet 3 |
| 8 | 109,085 | 109,137 | 109,412 | 109,210 | −0.047 | −0.298 | −0.114 |
| 9 | 112,149 | 112,181 | 111,910 | 112,150 | −0.028 | 0.213 | −0.00089 |
| 11 | 122,562 | 122,629 | 121,525 | 121,810 | −0.054 | 0.853 | 0.617 |
| 13 | 123,821 | 123,870 | 123,805 | 124,115 | −0.039 | 0.013 | −0.237 |
| 14 | 131,627 | 131,655 | 131,220 | 131,830 | −0.021 | 0.310 | −0.154 |
| 15 | 137,425 | 138,480 | 138,505 | 138,155 | −0.762 | −0.779 | −0.528 |

$\bar{f}^*$ and $\bar{f}^c$ are the finite element resonance frequency vectors corresponding to $\bar{p}^*$ and $\bar{p}^c$, respectively. $\bar{f}_1^e$, $\bar{f}_2^e$, $\bar{f}_3^e$ are the finite element resonance frequency vectors, upon completion of sensitivity analysis, corresponding to $\bar{p}_1^e, \bar{p}_2^e, \bar{p}_3^e$ of Tablet 1, Tablet 2, Tablet 3, respectively. $\bar{f}_{v_1}^e, \bar{f}_{v_2}^e, \bar{f}_{v_3}^e$ are the experimental resonance frequency vectors directly measured with the vacuum wand for Tablet 1, Tablet 2, Tablet 3.

Figure 9:
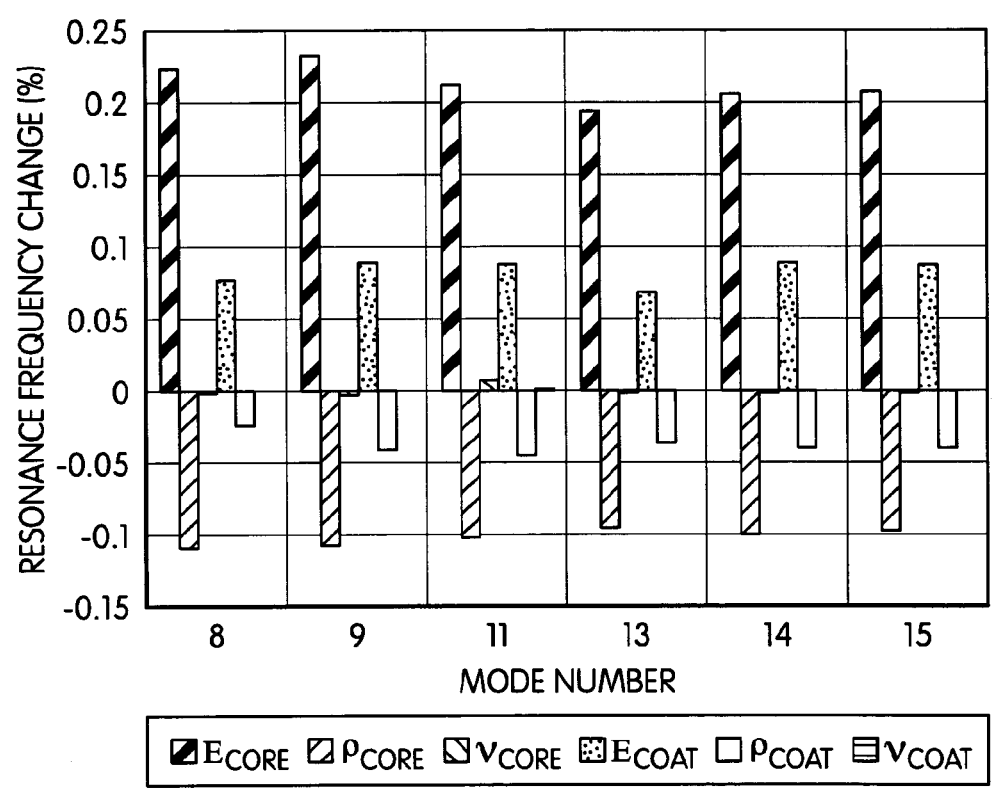
FIG. 9 illustrates the normalized sensitivities of the resonance frequencies of Tablet 1 to the changes in Ecore, ρcore, vcore, Ecoat, ρcoat, and vcoat for the modes 8, 9, 11, 13, 14 and 15.
Figure 10A:
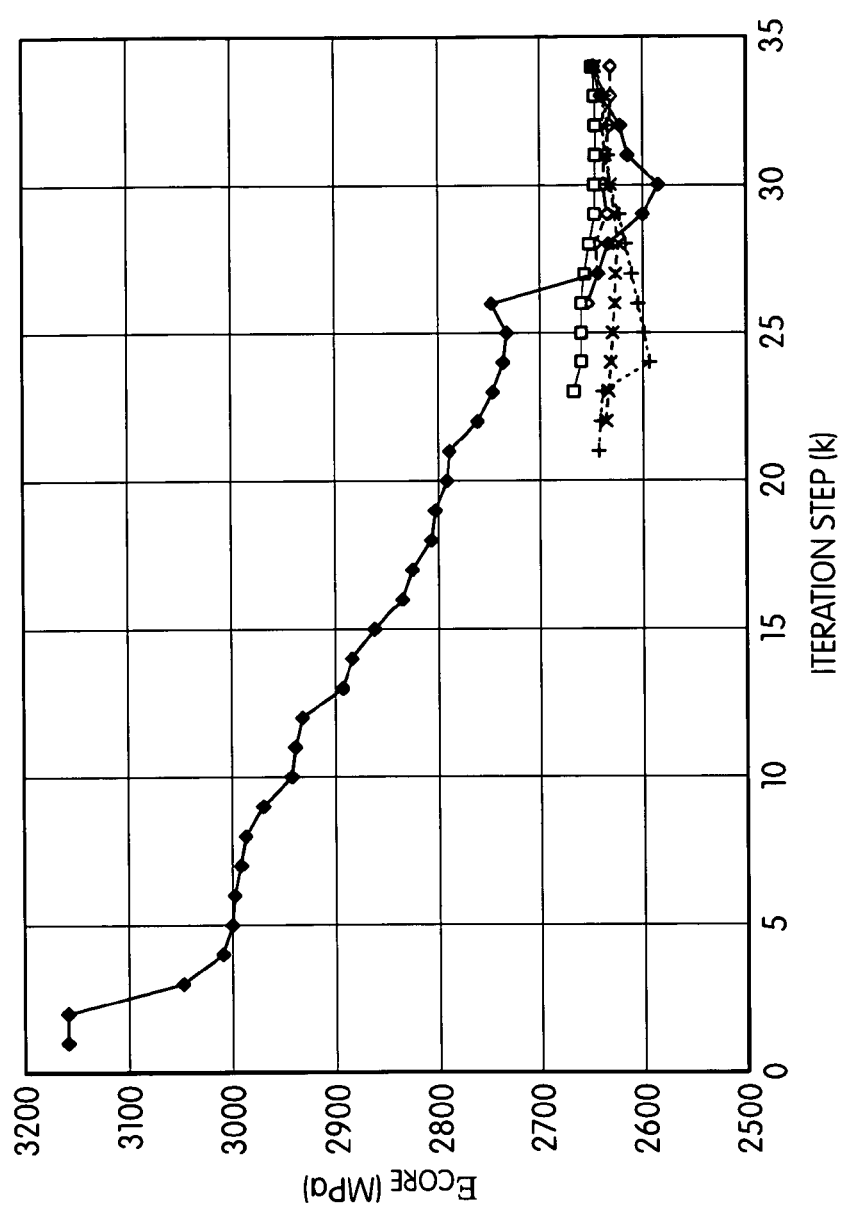
FIG. 10 illustrates the convergence of Ecore (a), ρcore (b), vcore (c), Ecoat (d), ρcoat (e), and vcoat (e) of the Tablet 1 during the sensitivity iterations.
Figure 10B:
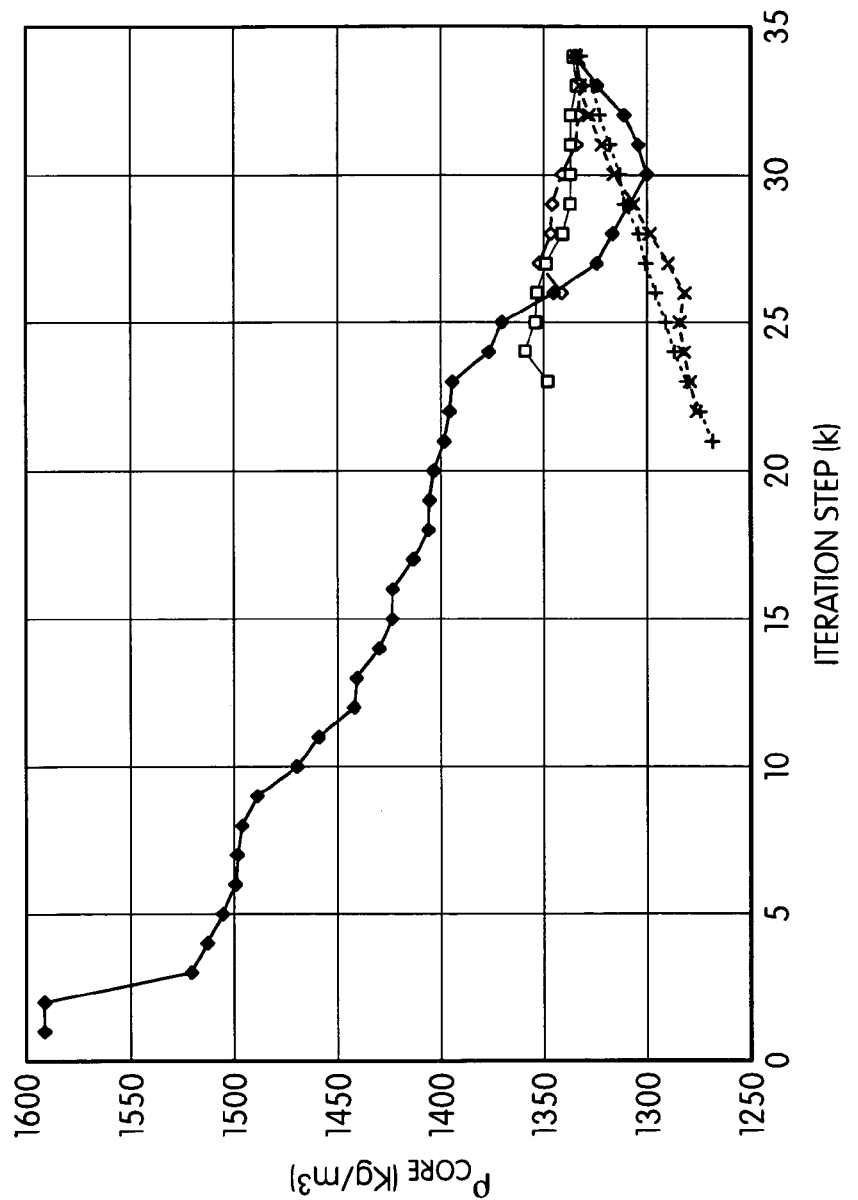
Figure 10C:
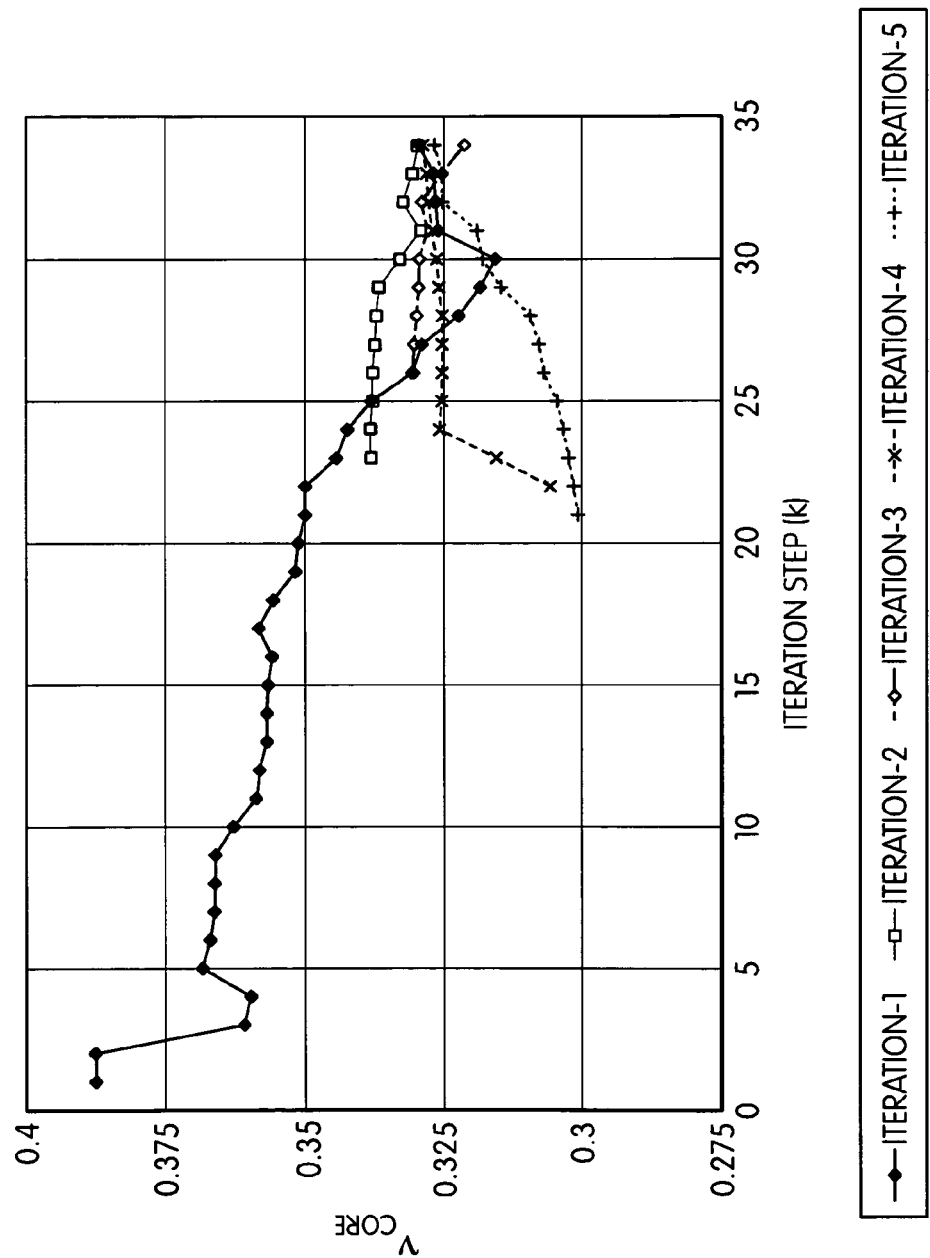
Figure 10D:
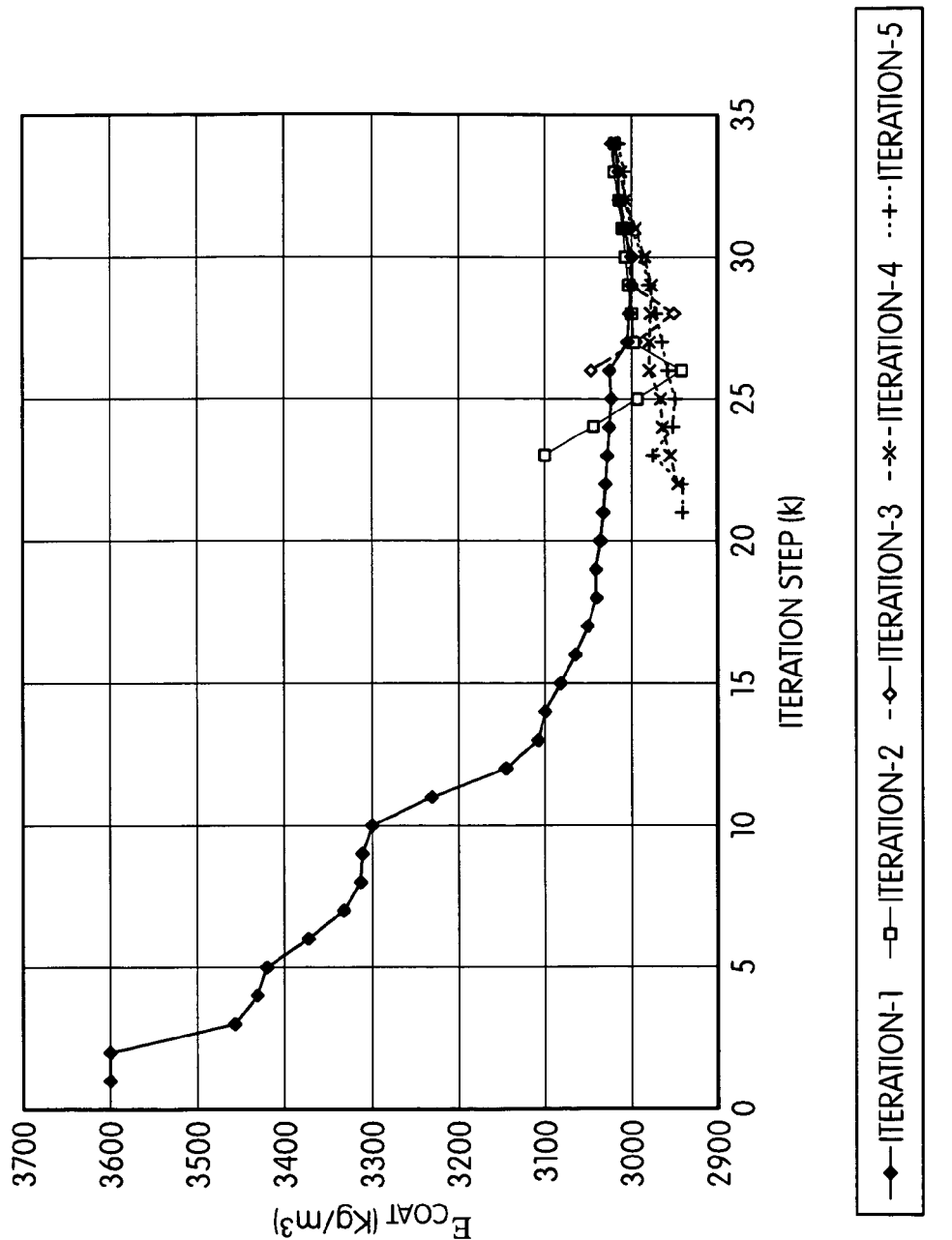
Figure 10F:
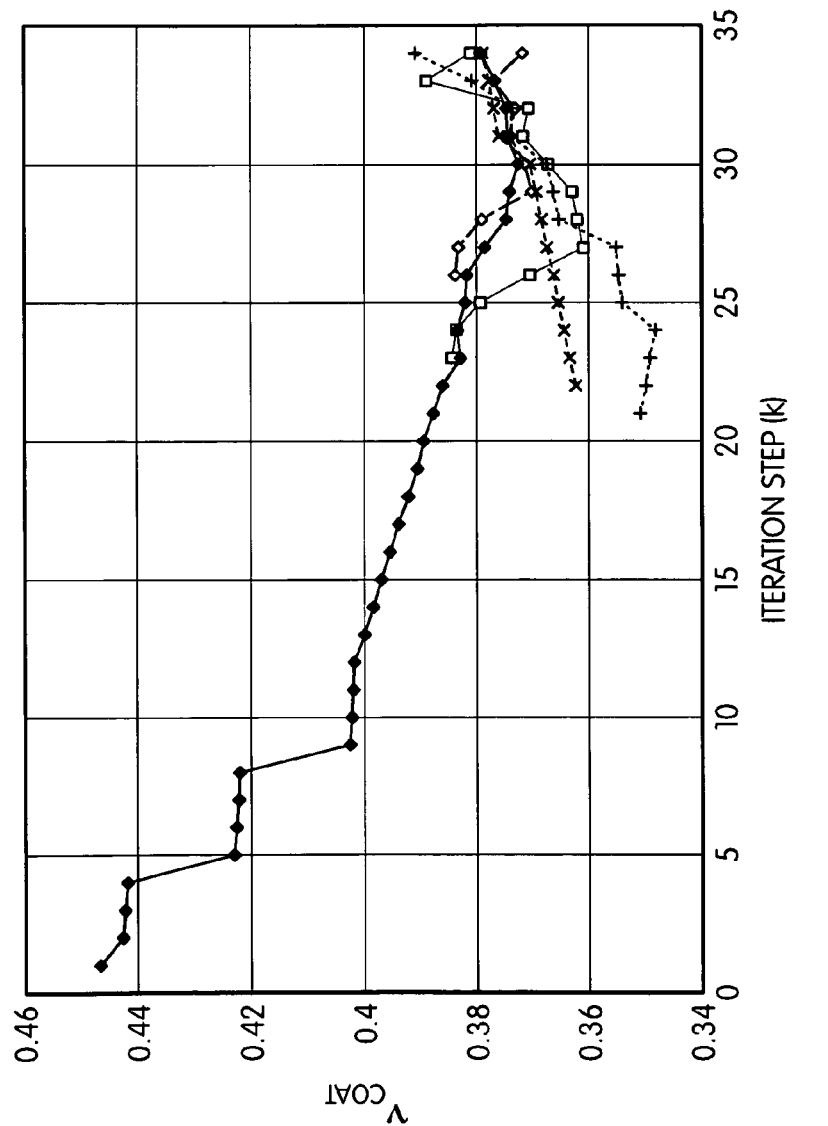

The sensitivity order of resonance frequencies regarding changes in mechanical properties from most to least sensitive are; $E_{core}$, $\rho_{core}$, $E_{coat}$, $\rho_{coat}$, $v_{core}$ and $v_{coat}$ (See FIG. 9). Convergence of the mechanical property parameters of Tablet 1 in the iterative loop is depicted in FIG. 8. Local convergence of each mechanical property is also illustrated in FIG. 10.

Conclusions and Remarks

In the present disclosure, a non-destructive/non-contact testing platform for determining the mechanical properties of drug tablets has been described. A computational procedure for extracting mechanical property parameters from measured resonance frequencies of tablets is developed and implemented. The effectiveness of the procedure for extracting the mechanical properties (Young's modulus, Poisson's ratio and mass density) of a core and coating layer of tablets from a set of experimentally obtained resonance frequencies is demonstrated. A main conclusion is that mechanical properties can be extracted utilizing the discussed experimental methodology and the iterative computational procedure based on subsets of the resonance frequencies of the tablet. Acquired experimental resonance frequencies agree quantitatively well with the finite element-based resonance frequencies corresponding to the extracted mechanical properties. Analysis also revealed that resonance frequencies of a sample tablet are most sensitive to changes in $E_{core}$, and least sensitive to changes in $v_{coat}$.

The principal applications of the methods and apparatuses disclosed include (i) real-time quality and mechanical integrity of tablet during compaction, (ii) real-time characterization of tablet property determination during compaction, and (iii) specialized defect detection and characterization methods of drug tablets.

Figure 12A:
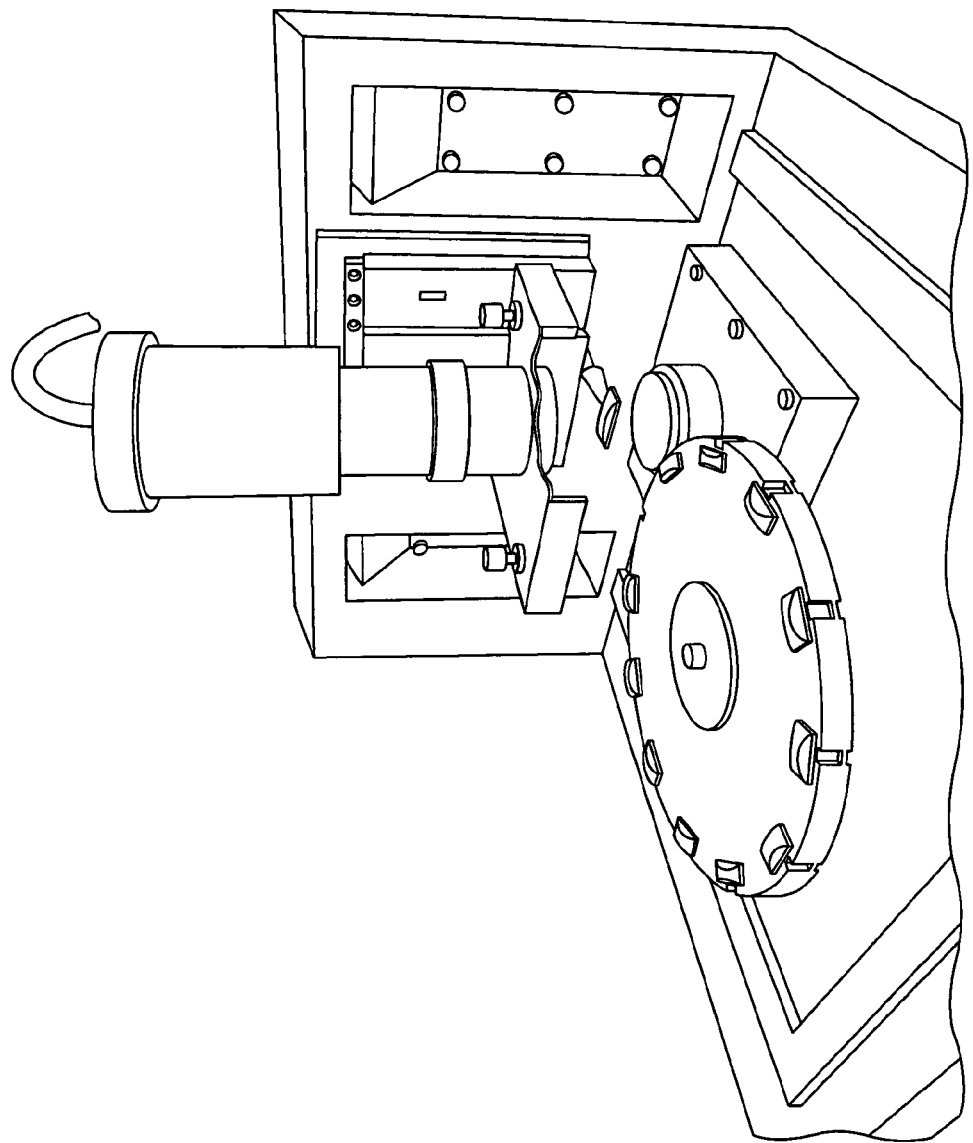
FIGS. 12(*a*) and (*b*) illustrate examples of potential uses of the tablet monitoring evaluation platform including a desktop testing unit and an online monitoring system.
Figure 12B:
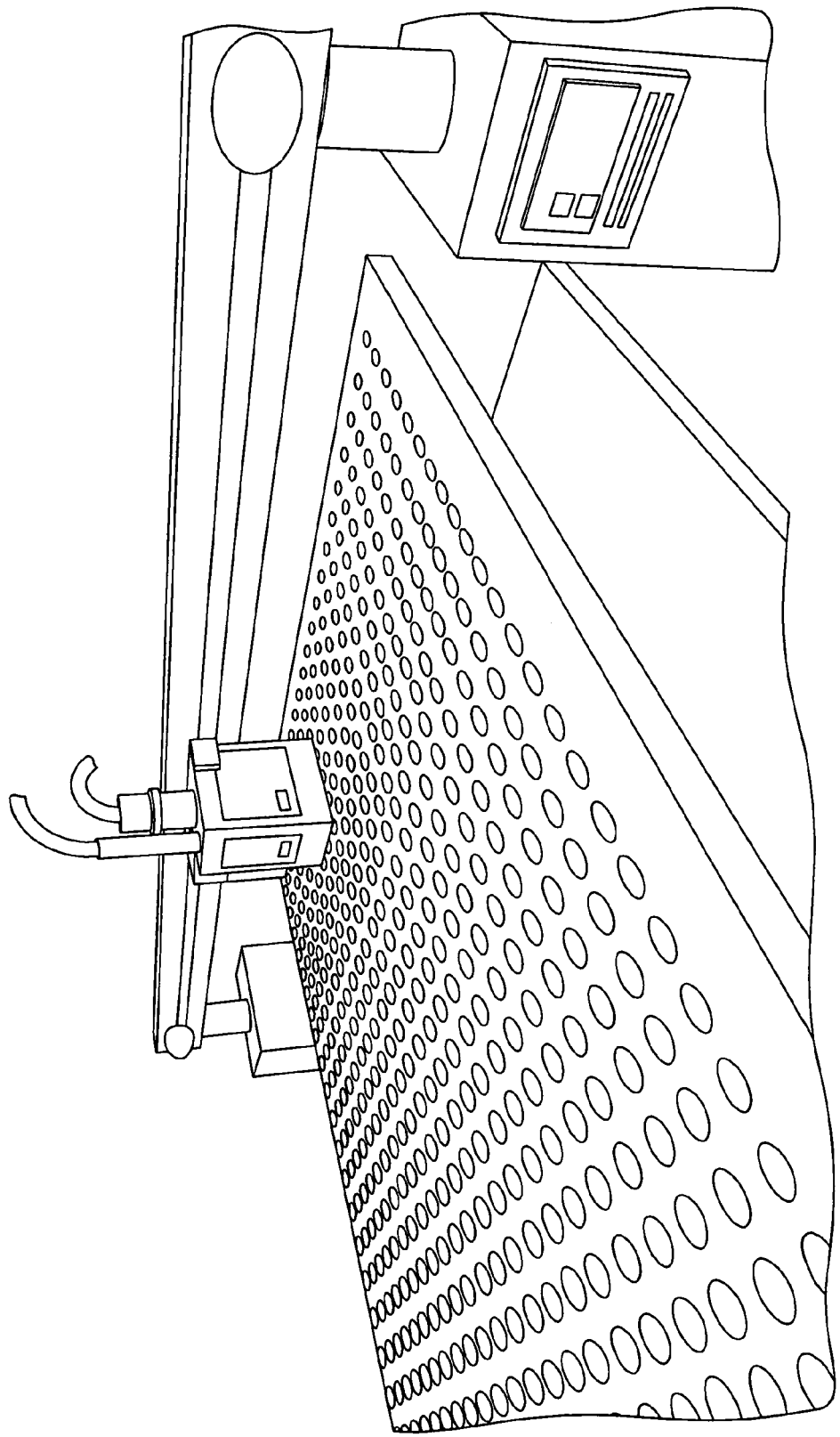
Figure 13:
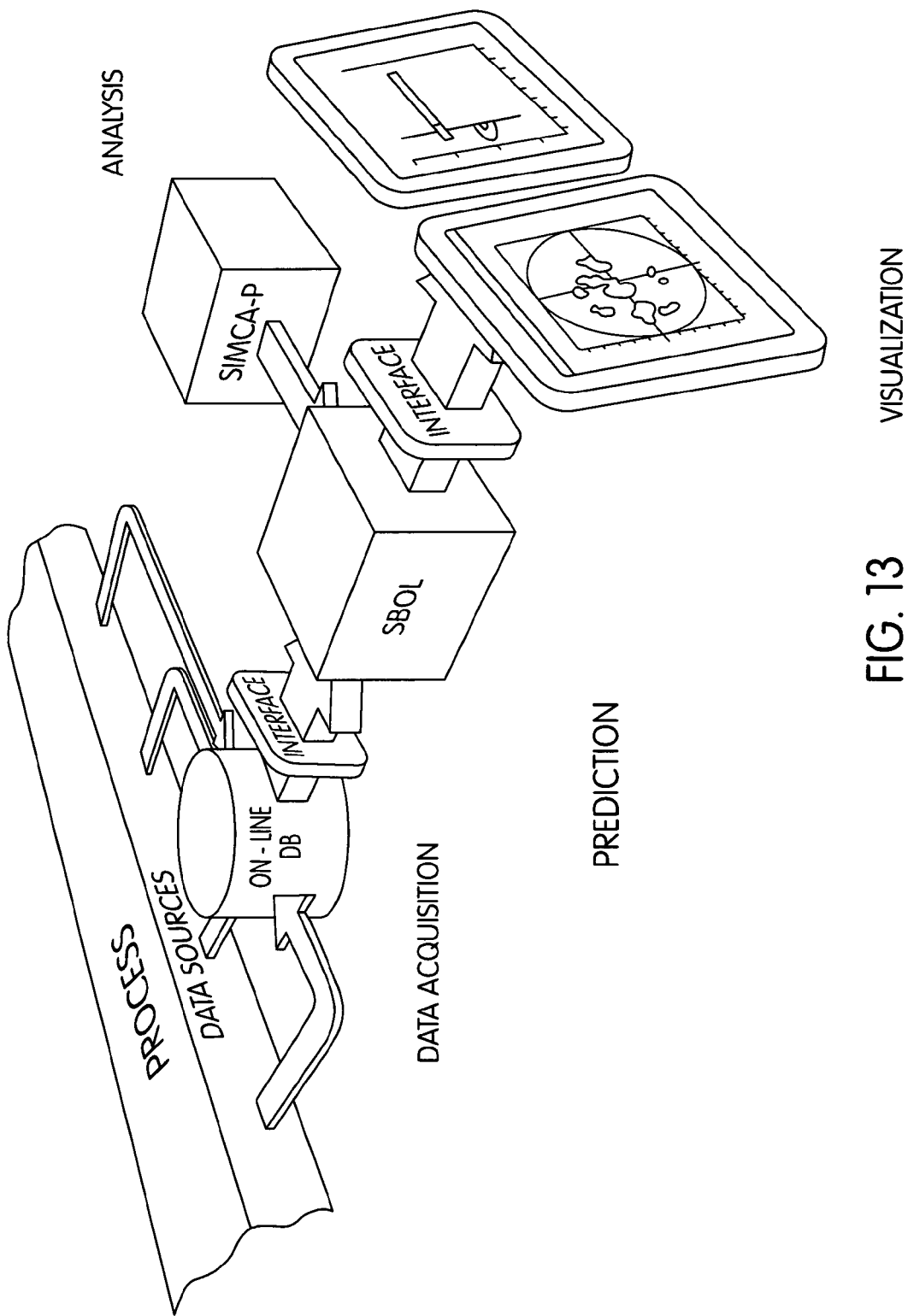
FIG. 13 illustrates a connectivity diagram of various components of a monitoring system.

FIG. 12 illustrates examples of potential uses of the tablet monitoring/evaluation platform including a design of a desktop testing unit and an online monitoring system. FIG. 13 illustrates a connectivity diagram of various components of a typical monitoring system. The functions of the tablet monitoring/evaluation platform can be integrated into an existing system.

The illustrative embodiments and modifications thereto described hereinabove are merely exemplary. It is understood that other modifications to the illustrative embodiments will readily occur to persons of ordinary skill in the art. All such modifications and variations are deemed to be within the scope and spirit of the present invention as will be defined by the accompanying claims.

REFERENCES

The following references and all references cited above are hereby incorporated herein by reference.

P. M. Morse and K. U. Ingard, Theoretical Acoustics, Princeton University Press, 1968.
J. Krautkramer and K. Krautkramer, Ultrasonic Testing of Materials, Springer-Verlag, 1990.
The specification list for the Presster compaction simulator, Metropolitan Computing Corporation, www.mcc-online.com.
B. A. C. Carlin, the Future of Compaction, *Pharmaceutical Technology*, June, 2004.
I. Varghese, L. Ban, M. D. M. Peri, Li C, G. Subramanian, C. Cetinkaya, Non-contact Drug Tablet Monitoring, Control Engineering, 53 (2), 2006.
Ivin Varghese and Cetin Cetinkaya, Non-contact Photoacoustic Defect Detection in Drug Tablets, submitted for publication in the Journal of Pharmaceutical Sciences., 2006.
Berkovich, E. S., 1951. Three-Faceted Diamond Pyramid for Micro-Hardness Testing. Industrial Diamond Review, 11, 129-132.
Jetzer W., Leuenberger H., Sucker H., 1983. The compressibility and compatibility of pharmaceutical powders. Pharmaceutical Technology, 7, 33-39.
Fell J. T., Newton, J. M., 1968. Tensile strength of lactose tablets. The Journal of Pharmacy and Pharmacology, 20, 657-659.

Fell J. T., Newton, J. M., 1970. The prediction of the tensile strength of tablets. The Journal of Pharmacy and Pharmacology, 22, 247.

Hancock, B. C., Colvin, J. T., Mullarney, M. P. Zinchuk, A. V., 2003. The relative densities of pharmaceutical powders, blends, dry granulations, and immediate-release tablets. Pharmaceutical Technology, 27, 64-80.

Payne R. S., Roberts R. J., Rowe R. C., McPartlin M., Bashall A., 1996. The mechanical properties of two forms of primidone predicted from their crystal structures. International Journal of Pharmaceutics, 145, 165-173.

Roberts R. J., Payne R. S., Rowe R. C., 2000. Mechanical property predictions for polymorphs of sulphathiazole and carbamazepine. European Journal of Pharmaceutical Sciences, 9, 277-283.

Roberts R. J., Rowe R. C., 1987. The Young's modulus of pharmaceutical materials. International Journal of Pharmaceutics, 37, 15-18.

Bassam F., York P., Rowe R. C., Roberts R. J., 1990. Young's modulus of powders used as pharmaceutical excipients. International Journal of Pharmaceutics, 64, 55-60.

Rigdway K., Aulton M. E., 1970. The surface hardness of tablets, Journal of Pharmacy and Pharmacology, 22, 70-78.

Felton L. A., Shah N. H., Zhang G., Infeld M. H., Malick A. W., McGinity J. W., 1996. Physical-mechanical properties of film-coated soft gelatin capsules. International Journal of Pharmaceutics, 127, 203-211.

Stanley P., Rowe R. C. and Newton J. M., 1981. Theoretical considerations of the influence of polymer film coatings on the mechanical strength of tablets. Journal of Pharmacy and Pharmacology, 33, 557-560.

Gutierrez-Rocca J. C. and McGinity J. W., 1993. Influence of aging on the physical-mechanical properties of acrylic resin films cast from aqueous dispersions and organic solutions. Drug Development and Industrial Pharmacy, 19, 315-332.

Gutierrez-Rocca J. C. and McGinity J. W., 1994. Influence of water soluble and insoluble plasticizers on the physical and mechanical properties of acrylic resin copolymers. International Journal of Pharmaceutics, 103, 293-301.

Obara S, and McGinity J. W., 1994. Properties of free films prepared from aqueous polymers by a spraying technique. Pharmaceutical Research, 11, 1562-1567.

Wong D. Y. T., Waring M. J., Wright P. and Aulton M. E., 1991. Elucidation of the compressive deformation behavior of α-lactose monohydrate and anhydrous α-lactose single crystals by mechanical strength and acoustic emission analyses. International Journal of Pharmaceutics, 72, 233-241.

Waring M. J., Rubinstein M. H., Howard J. R., 1987. Acoustic emission of pharmaceutical materials during compression. International Journal of Pharmaceutics, 36, 29-36.

Hakanen A., Laine E., 1993. Acoustic emission during powder compaction and its frequency spectral analysis. Drug Development and Industrial Pharmacy, 19, 2539-2560.

Hakanen A., Laine E., 1995. Acoustic Characterization of a micro-crystalline cellulose powder during and after its compression. Drug Development and Industrial Pharmacy, 21, 1573-1582.

Serris E., Camby-Perier L., Thomas G., Desfontaines M., Fantozzi G., 2002. Acoustic Emission of Pharmaceutical Powders during Compaction, Powder Technology, 128, 2-3, 296-299.

Hardy I. J. and Cook W. G., 2003. Predictive and correlative techniques for the design, optimization and manufacture of solid dosage forms. Journal of Pharmacy and Pharmacology, 55 (1), 3-18.

Morisseau K. M., Rhodes C. T., 1997. Near-infrared spectroscopy as a non-destructive alternative to conventional tablet hardness testing. Pharmaceutical Research, 14 (1), 108-111.

Kirsch J. D., Drennen J. K., 1999. Nondestructive tablet hardness testing by near-infrared spectroscopy: a new and robust spectral best-fit algorithm. Journal of Pharmaceutical and Biomedical Analysis, 19 (3-4), 351-362.

Chen Y. X., Thosar S. S., Forbess R. A., Kemper M. S., Rubinovitz R. L., Shukla A. J., 2001. Prediction of drug content and hardness of intact tablets using artificial neural network and near-infrared spectroscopy. Drug Development and Industrial Pharmacy, 27 (7), 623-631.

Donoso M., Kildsig D. O., Ghaly E. S., 2003. Prediction of tablet hardness and porosity using near-infrared diffuse reflectance spectroscopy as a nondestructive method. Pharmaceutical Development and Technology, 8 (4), 357-366.

Blanco M., Alcala M., 2006. Content uniformity and tablet hardness testing of intact pharmaceutical tablets by near infrared spectroscopy—A contribution to process analytical technologies. Analytica Chimica Acta, 557 (1-2): 353-359.

Otsuka M., Yamane I., 2006. Prediction of tablet hardness based on near infrared spectra of raw mixed powders by chemometrics. Journal of Pharmaceutical Sciences, 95, 1425-1433.

Saltelli A., Trantola S., Campolongo F., Ratto M., 2004. Sensitivity Analysis in Practice, a Guide to Assessing Scientific Models. Joint Research Centre of the European Commission, John Wiley & Sons, Ltd. pp. 42-47.

Akseli I., Libordi C. F., Cetinkaya C., 2006. Non-contact Mechanical Property Determination of Drug Tablets, Submitted, Journal of Pharmaceutical Sciences Akseli I., Cetinkaya C., Becker D., 2007. Ultrasonic Determination of Young's Moduli of the Coat and Core Materials of a Drug Tablet. In preparation for publication in the Journal of Pharmaceutical Sciences.

Behncke H. H., 1984. Coating thickness measurement by the X-ray fluorescence method. Metal Finishing, 82, no. 5, 33-39.

Cetinkaya C., Akseli I., Mani G. N., Libordi C. F., Varghese I., 2006. Non-contact mechanical characterization and testing of drug tablets, Advanced Ultrasonic Methods for Material and Structure Inspection, edited by T. Kundu, ISTE Science and Technical Publishing, UK, 319-369.

Felton L. A., 2003. Recent Advances in the Study of Polymeric Film Coating, AAPS News Magazine, 24-26.

Fitzgerald A. J., Cole B. E., Taday P. F., 2005. Nondestructive Analysis of Tablet Coating Thicknesses Using Terahetz Pulsed Imaging. Journal of Pharmaceutical Science, 94, 177-183.

Hussain A. S., Watts C., Afnan A. M., Wu H., 2004. Foreword. Journal of Process Analytical Technology, 1, 3.

Mathiowitz E., 1999. Encyclopedia of Controlled Drug Delivery—Volumes 1-2, John Wiley & Sons, 729-742.

Mowery M. D., Sing R., Kirsch J., Razaghi A., Bechard S., Reed R. A., 2002. Rapid at-line analysis of coating thickness and uniformity on tablets using laser induced breakdown spectroscopy. Journal of Pharmaceutical and Biomedical Analysis, 28, 935-943.

I claim:

1. A method of detecting, monitoring or characterizing a drug tablet comprising of one or more components/parts during compaction comprising the acts of:

forming a tablet from a core comprising powder or other solid components in a compactor;

transmitting a first set of acoustic waves into said core while said tablet is being formed;
receiving a second set of said acoustic waves from said core while said tablet is being formed;
measuring data received from said received acoustic waves;
coupling devices that transmit and receive and devices that measure said data within instrumentation and signal processing system;
using said instrumentation and signal processing system for transmitting/receiving said data with wire and/or wireless means;
using a computer for calculating said data;
presenting said calculated data on a display device; and
transmitting said calculated data after processing to a control unit of said compactor as process feedback with wire and wireless means,
wherein said method determines a quality level of said drug tablet and/or a defect state of a tablet from said calculated data.

2. The method of claim 1 wherein said acoustic waves both pressure and shear are generated and received by pressure (longitudinal) and shear (transverse) transducers embedded in a die and one or more punches of said compactor.

3. The method of claim 2 wherein said instrumentation comprises:
a pulser/receiver unit, coupled to a non-contact transducer and a digitizing oscilloscope or a digitizing oscilloscope or board;
wired or wireless transmitter and receiver units; and
a computer and a computer program product coupled to a camera and said digitizing oscilloscope or digitizing board.

4. The method of claim 1 wherein a computer program product is used with said instrumentation and signal processing for detecting, monitoring or characterizing a drug tablet during compaction the computer program product comprising:
a non-transitory computer usable medium having computer readable program code embodied in said medium for directing said detecting, monitoring or characterizing a drug tablet during compaction, wherein said detecting, monitoring or characterizing includes transmitting pressure (longitudinal) and shear (transverse) acoustic waves into said core while said tablet is being formed;
receiving acoustic waves from said core while said tablet is being formed;
acquiring data received from said received acoustic waves;
transmitting/receiving of said data with wire and wireless means:
calculating and analyzing said data;
presenting said calculated data and;
transmitting said calculated and analyzed data after processing to said control unit of said compactor as process with wire and/or wireless means.

5. The method of claim wherein said characterizing comprises:
determining Young's modulus; Poisson's ratios; material mass densities of said tablet components; mechanical defect state and a quality level of said tablet and/or its components.

6. The method of claim 1 wherein said characterizing comprises:
determining geometric characteristics further comprising tablet coating layer thickness: component layer thickness; uniformity of thickness distribution; geometric defect state and quality level of said tablet and/or its components.

7. An apparatus for detecting, monitoring or characterizing the components/parts of a drug tablet during compaction comprising:
a compactor having a plurality of punches and die;
means for forming a tablet from a core comprising of powder or other solid components within said compactor;
a first plurality of transducers within said compactor for transmitting acoustic waves into said core while said tablet is being formed;
a second plurality of transducers for within said compactor receiving acoustic waves from said core while said tablet is being formed;
instrumentation and signal processing coupled to said transducers for transmitting/receiving of data with wire or wireless means; and
measuring, calculating, transmitting and presenting said data wherein said device determines a quality level of said drug tablet and/or a defect state of a tablet from said calculated data.

8. The apparatus of claim 7 wherein said transducers for transmitting acoustic signal waves to said core comprising of one or more components/parts and said transducers for receiving acoustic waves from said core are a single transducer performing both functions.

9. A method of determining characteristics of components of a tablet comprising the acts of:
exciting said tablet with an acoustic and/or thermal field during compaction of said tablet;
acquiring reflected acoustic and or thermal signals from said tablet;
transmitting/receiving of data with wire or wireless means
instrumentation and signals processing coupled to transducers for transmitting/receiving of said data with wire or wireless means;
transmitting said signals after processing to a control unit of a compactor as process feedback with wire or wireless means;
digitizing said reflected signals;
measuring and calculating said digital signals;
extracting thermal state, mechanical and geometric characteristics as well as a quality level and tablet defect state from said digitized signals having resonance frequencies within a certain bandwidth.

10. The method of claim 9 wherein said exciting comprises vibrating said tablet.

11. The method of claim 9 wherein acquiring of surface vibration signal comprises detecting a shift of a reflected laser beam from said surface with an interferometer.

12. The method of claim 9 wherein digitizing said surface vibration signal is performed by an oscilloscope or digitizing board.

13. The method of claim 9 wherein said digitizing said reflected signal is performed by a sampling (digitizing) board.

14. The method of claim 9 wherein said extracting said mechanical characteristics from said digitized signals having resonance frequencies within a certain bandwidth is achieved, using an iterative process.

15. The method of claim 14 wherein said iterative process is performed by a computer using a computer program product.

16. The method of claim 15 wherein said computer program product is used for determining mechanical characteristics and geometric properties of a tablet and/or it components as well as its defect state said computer program product comprising:

anon-transitory computer usable medium having computer readable program code embodied in said medium for determining said thermal state, mechanical characteristics and geometric properties wherein said determining said mechanical characteristics and geometric properties includes exciting said tablet with an acoustic field or thermal field;

acquiring reflected signals from said tablet surfaces;

digitizing said reflected signals; and extracting said thermal state mechanical characteristics and geometric properties as well as a quality level defect state from said resonance frequencies within a certain bandwidth.

17. The method of claim 9 when said mechanical characteristics further comprise:

Young's modulus;

Poisson's ratios:

material mass densities of tablet components: and mechanical defect state of said tablet and/or its components.

18. The method of claim 9 where said mechanical further comprises:

tablet coating layer thickness;

component layer thickness;

uniformity of thickness distributions; and geometric defect state of said tablet and/or its components.

19. The method of claim 9 wherein acquiring of a surface vibration signal uses a transducer.

20. An apparatus for non-contact mechanical property characterization of drug tablets comprising:

a pulser/receiver unit coupled to an air-coupled transducer;

a thermal source;

an acoustic field generated on an active surface of said transducer interacts with a tablet mounted on a vacuum wand and the tablet's vibrational modes are excited;

an interferometer embedded within a microscope measures a transient out-of-plane motion of a particular point on a surface of said vibrating tablet; and a camera coupled to an output of said interferometer is coupled to measurement and calculation instrumentation;

and wherein a vacuum control unit and said vacuum wand retrieve and support said tablets to be characterized, further wherein said interferometer or contact and/or non-contact transducer measures a vibrational response from an excited tablets, and further wherein said, instrumentation transmits/receives wirelessly, digitizes and performs an iterative calculation of said vibrational responses to determine thermal and mechanical characteristics and geometric properties as well as quality and defect state of said tablet and or its components;

further wherein transmitting data after processing to said control unit of compactor as process feedback with wire and/or wireless means.

21. The apparatus of claim 20 wherein said instrumentation further comprises a computer and a computer program product for determining said mechanical characteristics and geometric properties of said tablets.

22. The apparatus of claim 21 wherein said computer program comprises an iterative process.

* * * * *